United States Patent
Czech et al.

(10) Patent No.: US 6,221,841 B1
(45) Date of Patent: Apr. 24, 2001

(54) GENERAL RECEPTORS FOR PHOSPHOINOSITIDES AND USES RELATED THERETO

(75) Inventors: Michael P. Czech, Wrentham; Jes K. Klarlund, Worcester, both of MA (US)

(73) Assignee: University of Massachusetts Medical Center, Worcester, MA (US)

( * ) Notice: Subject to any disclaimer, the term of this patent is extended or adjusted under 35 U.S.C. 154(b) by 0 days.

(21) Appl. No.: 08/729,834

(22) Filed: Oct. 7, 1996

(51) Int. Cl.$^7$ .............................. A61K 38/00; C07K 1/00; C07H 21/02
(52) U.S. Cl. .......................... 514/12; 530/350; 536/23.1
(58) Field of Search .............................. 530/350; 514/12; 536/23.1

(56) References Cited

FOREIGN PATENT DOCUMENTS

WO 9529673    11/1995   (WO) .
WO 9739124    10/1997   (WO) .

OTHER PUBLICATIONS

Hammonds–Odie, Latanya P. et al. "Identification and Cloning of Centaurin–α" *The Journal of Biological Chemistry* 271 (31):18859–18868 (1996).

Achstetter, T. et al., "SEC7 Encodes an Unusual, High Molecular Weight Protein Required for Membrane Traffic from the Yeast Golgi Apparatus", (1988) *J. Biol. Chem.* 263(24):11711–11717.

Akiyama, S.K., et al., "Fibronectin and integrins in invasion and metastasis", (1995) *Cancer and Metastasis Reviews* 14:173–189.

Czech, M.P., "Molecular Actions of Insulin on Glucose Transport", (1995) *Annu. Rev. Nutr.* 15:441–71.

Downward, J., "A target for PI(3) kinase", (1995) *Nature* 376:553–554.

Franke, T.E. et al., "The Protein Kinase Encoded by the Akt Proto–Oncogene Is A Target of the PDGF–Activated Phosphatidylinositol 3–Kinase", (1995) *Cell* 81:727–736.

Harlan, J.E. et al., "Pleckstrin homology domains bind to phosphatidylinositol–4,5–bisphosphate", (1994) *Nature* 371:168–170.

Hynes, R.O., "Integrins: Versatility, Modulation, and Signaling in Cell Adhesion", (1992) *Cell* 69:11–25.

Kolanus, W. et al., "αLβ2 Integrin/LFA–1 Binding to ICAM–1 Induced by Cytohesion–1, a Cytoplasmic Regulatory Molecule", (1996) *Cell* 86:233–242.

Lemmon, M.A. et al., "Specific and high–affinity binding of inositol phosphates to an isolated pleckstrin homology domain", (1995) *Proc. Natl. Acad. Sci. USA* 92:10472–76.

Liu, L. and B. Pohadjak, "Cloning and sequencing of a human cDNA from cytolytic NK/T cells with homology to yeast SEC7", (1992) *Biochim. et Biophys. Acta. 1132*:75–78.

Lub, M. et al., "Ins and outs of LFA–1", (1995) *Immunol. Today 16(10)*:479–483.

Pawson, T., "Protein nodules and signalling networks", (1995) *Nature 363*:573–580.

Rawlings, D.J. et al. "Mutation of Unique Region of Bruton's Tyrosine Kinase in Immunodeficient XID Mice", (1993) *Science 261*:358–361.

Simmons, D. et al., "ICAM, an adhesion ligand of LFA–1, is homologous to the neural cell adhesion molecule NCAM", (1988) *Nature 331*:624–627.

Tang, D.G. and K.V. Honn, "Adhesion Molecules and Tumor Metastasis: An Update", (1994–1995) *Invasion Metastasis 14*:109–122.

*Primary Examiner*—Rebecca E. Prouty
*Assistant Examiner*—M. Monshipouri
(74) *Attorney, Agent, or Firm*—Lahive & Cockfield, LLP

(57) ABSTRACT

The present invention relates to the discovery of a novel isoform of phosphatidylinositide binding protein, referred to herein a "general receptors for phosphoinositides" or "GRPs". The GRP molecules show a modular structure comprising a domain homologous to the yeast SEC7 gene product and a pleckstrin homology (PH) domain. GRP proteins exhibit specific high affinity binding to products of the lipid kinase phosphatidylinositol-3-OH kinase, such as phosphotidylinositol-3,4,5. As described herein, GRP proteins may function as adaptors between membrane signalling and multiple downstream targets. Thus, GRP polypeptides potentially mediate multiple signalling events such as cell adhesion and membrane trafficking, among others. This invention describes isolated and antisense nucleic acids molecules, recombinant expression vectors containing a nucleic acid molecule of the invention, host cells into which the expression vectors have been introduced and non-human transgenic animals in which GRP gene has been introduced or disrupted. In addition, the invention provides isolated GRP proteins, fusion proteins, antigenic peptides and anti-GRP antibodies. Diagnostic, screening and therapeutic methods utilizing compositions of the invention are also provided. The invention further provides a method of cloning novel phosphatidylinositol binding protein.

15 Claims, 9 Drawing Sheets

|  | 10 | 20 | 30 | 40 | 50 |  |
|---|---|---|---|---|---|---|
|  | 1234567890 | 1234567890 | 1234567890 | 1234567890 | 1234567890 |  |
|  | ATGGACGAAG | GCGGTGGCGG | TGAGGGCGGC | AGCGTGCCTG | AAGACCTGTC | 50 |
|  | M D E G | G G E G | S V P | E D | L S |  |
|  | ATTAGAAGAG | CGAGAAGAAC | TTTTGGACAT | TCGTAGAAGA | AAAAAGGAAC | 100 |
|  | L E E | R E E L | L D I | R R R | K K E L |  |
|  | TTATTGATGA | CATTGAGAGG | CTGAAATATG | AAATTGCAGA | AGTGATGACG | 150 |
|  | I D D | I E R | L K Y E | I A E | V M T |  |
|  | GAGATTGACA | ACCTGACTTC | AGTGGAGGAG | AGCAAAACTA | CTCAGAGGAA | 200 |
|  | E I D N | L T S | V E E | S K T T | Q R N |  |
|  | CAAGCAAATA | GCCATGGGAA | GGAAGAAATT | CAACATGGAC | CCCAAAAAGG | 250 |
|  | K Q I | A M G R | K K F | N M D | P K K G |  |
|  | GCATTCAGTT | CCTAATTGAG | AACGACCTGC | TGCAGAGCTC | CCCAGAGGAT | 300 |
|  | I Q F | L I E | N D L L | Q S S | P E D |  |
|  | GTCGCCCAGT | TTCTGTACAA | AGGAGAGGGC | CTGAACAAGA | CCGTCATCGG | 350 |
|  | V A Q F | L Y K | G E G | L N K T | V I G |  |
|  | AGACTACCTG | GGTGAGAGGG | ATGACTTTAA | TATCAAAGTT | CTTCAGGCTT | 400 |
|  | D Y L | G E R D | D F N | I K V | L Q A F |  |
|  | TTGTTGAGCT | GCATGAGTTT | GCTGATCTCA | ACCTTGTCCA | GGCCTTAAGG | 450 |
|  | V E L | H E F | A D L N | L V Q | A L R |  |
|  | CAGTTCCTAT | GGAGCTTCAG | ACTTCCTGGA | GAGGCACAGA | AGATCGACCG | 500 |
|  | Q F L W | S F R | L P G | E A Q K | I D R |  |
|  | CATGATGGAG | GCCTTTGCAT | CCCGATACTG | CCTGTGCAAC | CCTGGGGTCT | 550 |
|  | M M E | A F A S | R Y C | L C N | P G V F |  |
|  | TCCAGTCCAC | AGATACATGC | TACGTGCTCT | CCTTTGCCAT | CATCATGCTC | 600 |
|  | Q S T | D T C | Y V L S | F A I | I M L |  |

*FIG. 1A*

```
          10         20         30         40         50
 1234567890 1234567890 1234567890 1234567890 1234567890
AACACCAGCT TGCACAACCA CAACGTGCGC GACAAGCCCA CCGCTGAGCG      650
 N  T  S  L  H  N  H  N  V  R  D  K  P  T  A  E  R

CTTCATCACC ATGAACCGAG GCATCAACGA GGGTGGGGAC CTTCCTGAGG      700
 F  I  T  M  N  R  G  I  N  E  G  G  D  L  P  E  E

AGCTGCTGAG GAACTTGTAT GAAAGTATCA AGAATGAGCC GTTTAAGATC      750
  L  L  R  N  L  Y  E  S  I  K  N  E  P  F  K  I

CCAGAAGACG ACGGAAATGA CCTGACACAC ACGTTCTTCA ACCCAGACCG      800
 P  E  D  D  G  N  D  L  T  H  T  F  F  N  P  D  R

AGAAGGCTGG CTGCTGAAGC TGGGGGGTCG TGTGAAGACC TGGAAACGGC      850
 E  G  W  L  L  K  L  G  G  R  V  K  T  W  K  R  R

GCTGGTTCAT CCTCACAGAT AACTGCCTCT ACTACTTTGA GTACACCACG      900
  W  F  I  L  T  D  N  C  L  Y  Y  F  E  Y  T  T

GACAAGGAGC CCAGGGGCAT CATCCCCCTG GAGAACCTCA GCATCAGGGA      950
 D  K  E  P  R  G  I  I  P  L  E  N  L  S  I  R  E

GGTGGAGGAC CCCCGGAAGC CGAACTGCTT TGAGCTGTAT AACCCCAGTC     1000
 V  E  D  P  R  K  P  N  C  F  E  L  Y  N  P  S  H

ACAAAGGTCA AGTCATCAAG GCCTGCAAGA CGGAGGCCGA TGGCCGTGTG     1050
  K  G  Q  V  I  K  A  C  K  T  E  A  D  G  R  V

GTGGAGGGCA ACCACGTTGT GTACCGGATC TCTGCCCCCA GCCCGGAGGA     1100
 V  E  G  N  H  V  V  Y  R  I  S  A  P  S  P  E  E

AAAGGAGGAG TGGATGAAGT CCATCAAAGC AAGCATCAGT AGGGACCCGT     1150
 K  E  E  W  M  K  S  I  K  A  S  I  S  R  D  P  F

TCTATGACAT GTTGGCCACG AGGAAAAGGA GGATTGCCAA TAAGAAATAG     1200
  Y  D  M  L  A  T  R  K  R  R  I  A  N  K  K
```

*FIG. 1B*

```
Grp1     MDEGGGGEGG  SVPEDLSLEE  REELLDIRRR  KKELIDDIER  LKYEIAEVMT  EIDNLTSVEE   60
EST01394 ----------  ----------  ----------  ---LIDDIER  LKYEIXEVMT  EIDNLTSVEE   56
B2-1/Ch-1 MEE----DOS YVPSDLTAEE  RQELENIRRR  KQELLADIQR  LKDEIAEVAN  EIENLGSTEE   56

Grp1      SKTTQRNKQI AMGRKKFNMD  PKKGIQFLIE  NOLLQSSPED  VAQFLYKGEG  LNKTVIGDYL  120
EST01394  SKTTQRXKQI AMGRKKFNMX  PKKGIQFLIE  NDLLQSSPED  VAQFLYKGEG  LNKTVIGDYL  116
B2-1/Ch-1 RKNMQRNKQV AMGRKKFNMD  PKKGIQFLIE  NDLLKNTCED  IAQFLYKGEG  LNKTAIGDYL  116

Grp1      GERDDFNIKV LQAFVELHEF  ADLNLVQALR  QFLWSFRLGP  EAQKIDRME   AFASRYCLCN  180
B2-1/Ch-1 GERDEFNIQV LHAFVELHEF  TDLNLVQALR  QFLWSFRLPG  EAQKIDRME   AFAQRYCQCN  176

Grp1      PGVFQSTDTC YVLSFAIIML  NTSLHNHNVK  DKPTAERFIT  MNRGINEGGD  LPEELLRNLY  240
B2-1/Ch-1 NGYFQSTDTC YVLSFAIIML  NTSLHNPNVK  DKPTVERFIA  MNRGINDGGD  LPEELLRNLY  236

Grp1      ESIKNEPFKI PEDDGNDLTH  TFFNPDREGV  LLKLGG-RVK  TWKRRWFILT  DNCLYFEYT   299
B2-1/Ch-1 ESIKNEPFKI PEDDGNDLTH  TFFNPDREGV  LLKLGGGRVK  TWKRRWFILT  DNCLYYFEYT  296

Grp1      TDKEPRGIIP LENLSIREVE  DPRKPNCFEL  YNPSHKGQVI  KACKTEADGR  VVEQNHVVYR  359
B2-1/Ch-1 TDKEPRGIIP LENLSIREVE  DSKKPNCFEL  YIPDNKDQVI  KACKTEADGR  VVEGNHTVYR  356

Grp1      ISAPSPEEKE ERMKSIKASI  SRDPFYDMLA  TRKRRIANKK  --                      399
B2-1/Ch-1 ISAPTPEEKE ERMKSIKAAI  SRDPFYEMLA  ARKKKVSSTK  RH                      398
```

FIG. 3B

```
Grp1        THTFFNPDRE   GNLLKLGG-R   VKTNKRRWFI   LTDNCLYYFE   YTTDKEPRGI
B2-1/Ch-1   THTFFNPDRE   GNLLKLGGGR   VKTWKRRWFI   LTDNCLYYFE   YTTDKEPRGI
SOS-1       GQCCNEFIME   GTL-----TR   VGAKHERHIF   LFDGLM----   -ICCKSNHGQ
IRS-1       TDGFSDVRKV   GYL-----RK   PKSMHKRFFV   LRAASE----   -AGGPARLEY

*            *

Grp1        IPLENLSIRE   VEDPRKPNCF   ELYNPSHKGQ   VIKACKTMAD   GRVVEGNHVV
B2-1/Ch-1   IPLENLSIRE   VEDSKKPNCF   ELYIPDNKDQ   VIKACKTEAD   GRVVEGNHTV
SOS-1       PRLPGASSAE   YRLKEKF--F   MRKVQINDKD   DTSEYKHAFE   IILKDGNSVI
IRS-1       YENEKKWRHK   SSAPKRS--I   PLESCFNINK   RADSKNKHLV   ALYTRDEHFA

Grp1        YRISAPSPEE   KEEWMKSIKA   SISRDPF
B2-1/Ch-1   YRISAPTPEE   KEEWIKCIKA   AISRDPF
SOS-1       F--SAKSAEE   KNNWMAALIS   LQYRSTL
IRS-1       I---AADSEAK   QDSWYQALLQ   LHNRAKA
```

*FIG. 5C*

GENERAL RECEPTORS FOR PHOSPHOINOSITIDES AND USES RELATED THERETO

FUNDING

Work described herein was supported by funding from the National Institutes of Health Grants DK30898 and DK30648. The U.S. government therefore may have certain rights in this invention.

BACKGROUND OF THE INVENTION

Stimulation of cells with extracellular signals results in the triggering of multiple signal transduction pathways. These pathways are cascades of information transfer that are initiated at the cell membrane and culminate in the nucleus, ultimately controlling gene expression, cellular proliferation and differentiation. One of these signalling systems involves the lipid kinases phosphatidylinositol-3-OH kinase, or PI(3)-kinases, which phosphorylate the hydroxyl group at position 3 on the inositol ring of phosphoinositides, a key activity that is switched on by a huge number of extracellular stimuli.

Multiple species of 3'-phosphorylated inositol lipids are thought to be involved in a number of cellular signaling and membrane trafficking pathways, including membrane ruffling (1), chemotaxis (3), secretory responses (3), membrane trafficking of growth factor receptors (4), insulin secretion, cell regulated adhesion (5) and insulin-mediated translocation of glucose transporters to the cell surface (reviewed in Czech (1995) *Annu. Rev. Nutri.* 15:441–471). A relatively large, constitutive pool of PI 3-phosphate is present in resting cells, while very low levels of PI 3,4-biphosphate and PI 3,4,5-triphosphate are rapidly increased in response to a number of external cellular stimuli (reviewed in Cantley et al. (1991) *Cell* 64:281–302 and Kapeller, R. and L. C. Cantley (1994) *Bioessays* 16:565–578). The pool of PI 3-phosphate may be largely due to PI (3)-kinases such as PtdIns 3-kinase (3), a mammalian homolog of the yeast VPS34 protein (Herman, P. K. and S. D. Emir (1990) *Mol. Cell. Biol.* 10:6742–6754), which can utilize only PI as substrate. In contrast, a second category of PI 3-kinases, isoforms of the p110 PI 3-kinase, are capable of phosphorylating PI 4-phosphate and PI 4,5-bisphosphate at the 3' position (Hiles et al. (1992) *Cell* 70:419–429; Hu et al. (1993) *Mol Cell. Biol.* 13:7677–7688; Kippel et al. (1994) *Mol. Cell. Biol.* 14:2676–2685; Stoyanov et al. (1995) *Science* 269:690–693). These enzymes apparently contribute to the regulated pools of PI 3,4-$P_2$ and PI-3,4,5-$P_5$ stimulated by receptor or non-receptor tyrosine kinase activation (in the case of isoforms p110 and p110β) or G protein activation (in the case of p110γ). The existence of multiple PI 3-kinase isoforms suggests the influence of multiple signaling pathways on these enzymes and, possibly, divergent reactions of the individual 3'-phosphoinositides.

Relatively little is known, however, about the mechanisms that transmit the signal beyond this point. Several groups have reported a novel protein module of approximately 100 amino acids termed the pleckstrin homology (PH) domain located at the carboxy-terminal of several proteins involved in signal transduction processes (Haslam et al. (1993) *Nature* 363:309–310; Mayer et al. (1993) *Cell* 73:629–630; Musacchio et al. (1993) *Trends Biochem. Sci.* 18:343–348). PH domains have been implicated in the binding to membranes containing PI 4,5-bisphosphate, as well as to the binding of several proteins βγ subunits (G βγ) of heterotrimeric G proteins (Touhara et al. (1994) *J. Biol. Chem.* 269:10217–10220; Satoshi et al. (1994) *Proc. Natl. Acad. Sci. USA* 91:11256–11260; Lemmon et al. (1995) *Proc. Natl. Acad. Sci. USA* 92:10472–10476), protein kinase C (Yao et al. (2994) *Proc. Natl. Acad. Sci. USA* 91:9175–9179), WD motifs (Wang et al. (1994) *Biochem. Biophys. Res. Commun.* 203:29–35). Although the three-dimensional structures of some PH domains have been resolved and some candidate ligands have been described, the precise determinants of PH domain-binding have not been established. It is uncertain whether all PH domains share a common ligand or whether there are differences between the PH domain that confer target specificity. Moreover, it is unclear whether 3'-phosphorylated inositol lipids act as ligands of PH domains, thus mediating the multiple signal transduction pathways triggered by (PI)3-kinases.

PH domains have been found in a number of proteins including protein kinase C α, phospholipase C-δ1, the serine/threonine kinase known variously as protein kinase B, Akt and Rac (Burgering, B. M. T. and P. J. Coffer (1995) *Nature* 376:599–602; Franke et al. (1995) *Cell* 81:727–736; Coffer, P. J. and J. R. Woodgett (1991) *Eur. J. Biochem.* 201:475–481) among others. Recently, cDNAs encoding a modular protein containing a domain homologous to the yeast SEC7 gene product and a PH domain have been reported (Liu, L. and B. Pohajdak (1992) *Biochim. Biophys. Acta* 1132:75–78; Kolanus et al. (1996) *Cell* 86:233–242). Full-length and SEC7 domain forms of these recently cloned molecules have been shown to induce b-β integrin-dependent binding of lymphoid cells to extracellular molecules such as ICAM-1 (Kolanus et al. (1996) supra). This finding implicates PH/SEC7 containing molecules not only in transducing extracellular signals into a cell, but in conveying information from the cell interior to the exterior via a mechanism termed "inside out signaling". In the immune system, inside out signaling has been associated with the orderly attachment of cells to their surrounding matrix, the adhesion of platelets to fibrinogen, the coupling of lymphocytes to their antigen presenting cells, and the phagocytosis of complement-opsonized targets by myelomonocytic phagocytes (reviewed by Diamond, M. S. and T. A. Springer (1993) *J. Cell. Biol.* 120:54556; Hynes (1992) *Cell* 69:11–25; and Sastry, S. K. and A. F. Horwitz (1993) *Curr. Opn. Cell. Biol.* 5:819–831).

Furthermore, SEC7 domains have also been implicated in glycoprotein secretion. SEC7 was originally identified in yeast as one of the at least 23 genes implicated in the process of intercompartmental protein transport (Novick, P. et al. (1981) *Cell* 25, 461–69; Novick, P. et al. (1980) *Cell* 21:205–157). Most of the SEC mutations block transport of proteins from the endoplasmic reticulum to the Golgi apparatus or from mature secretory vesicles to the plasma membrane (Esmon, B. et al. (1981) *Cell* 25:451–60; Stevens, T. et al. (1982) *Cell* 30: 439–48; Riezman, H. (1985) *Cell* 40: 1001–09). Mutations that define the sec7 locus exert a unique and dramatic effect on traffic of secretory, plasma membrane, vacuolar, and endocytic marker molecules (Novick et al. (1980) supra; Esmon et al. (1981) supra). At the restrictive growth temperature, sec7 mutant cells accumulate secretory glycoproteins within the Golgi apparatus, leading to the exaggeration of Golgi cisternae. The SEC7 gene has been cloned and shown to encode a large protein containing 2008 amino acids (Achstetter et al. (1988) *J. Biol. Chem.* 263(4):11711–11717).

There is evidence which suggests that compromise of PH domain function of Bruton's tyrosine kinase underlies the dysregulation of B cell ontogeny that is associated with the murine X-linked immunodeficiency syndrome (Rawlings et al. (1993) *Science* 261:358–361). Thus, identifying novel molecules that mediate some of these signaling events is critical in the understanding of these biological processes and in the development of therapeutic methods.

SUMMARY OF THE INVENTION

The present invention relates to the discovery of novel phosphatidylinositide binding proteins, referred to herein a "general receptors for phosphoinositide" or "GRPs". The GRP molecules show a functionally and structurally modular form which include a subdomain homologous to the yeast SEC7 gene product, and a pleckstrin homology (PH) domain. GRP proteins preferably exhibit high affinity binding to products of the lipid kinase phosphatidylinositol-3-OH kinase (referred to herein as PI(3)kinase), e.g., phosphatidylinositol-3,4,5 (PI-3,4,5). As described herein, GRP proteins may function as adaptors between membrane signalling and multiple downstream targets, thus mediating multiple signalling events such as cell adhesion and membrane trafficking, among others.

In one aspect, the invention provides isolated nucleic acid molecules encoding a GRP polypeptide. Such nucleic acid molecules (e.g., cDNAs) have a nucleotide sequence encoding a GRP polypeptide or biologically active portions thereof, such as a polypeptide having a GRP activity. In a preferred embodiment, the isolated nucleic acid molecule has a nucleotide sequence shown in FIG. 1, (SEQ ID NO: 1), or a portion thereof such as the coding region of the nucleotide sequence of FIG. 1, (SEQ ID NO: 1). Other preferred nucleic acid molecules encode a protein having the amino acid sequence of FIG. 3, (SEQ ID NO: 2). Nucleic acid molecules derived from adipocyte or muscle cells (e.g., a naturally-occurring nucleic acid molecule found in an adipocyte or muscle cell) which hybridize under stringent conditions to the nucleotide sequence shown in FIG. 1 (SEQ ID NO: 1) are also within the scope of the invention.

In another embodiment, the isolated nucleic acid molecule is a nucleotide sequence encoding a protein having an amino acid sequence which is at least about 80%, preferably at least about 85%, more preferably at least about 90% and most preferably at least about 91, 92, 93, 94, 95, 96, 97, 98, 99% overall amino acid sequence identity with an amino acid sequence shown in FIG. 3, (SEQ ID NO: 2). This invention further pertains to nucleic acid molecules which encode a protein which includes a pleckstrin homology (PH) domain having an amino acid sequence at least 85%, preferably at least 90%, more preferably at least 91, 91, 92, 93, 94, 95, 96, 97, 98, 99% identical to a PH domain of an amino acid sequence shown in FIG. 3, (SEQ ID NO: 2). Also within the scope of this invention are nucleic acid molecules which encode a protein which includes a SEC7 domain having an amino acid sequence at least 85%, preferably at least 87%, more preferably at least 88, 89, 90, 91, 91, 92, 93, 94, 95, 96, 97, 98, 99% identical to a SEC7 domain of an amino acid sequence shown in FIGS. 1 and 3, (SEQ ID NO: 2).

Nucleic acid molecules encoding proteins which include a PH domain having an amino acid sequence at least 80% (preferably at least 85%, or 90–99%) identical to a PH domain of an amino acid sequence shown in FIGS. 1 and 3, (SEQ ID NO: 2) and a SEC7 domain having an amino acid sequence at least 80% (preferably at least 85%, or 90–99%) identical to a SEC7 domain of an amino acid sequence shown in FIGS. 1 and 3, (SEQ ID NO: 2) are also within the scope of this invention.

Another aspect of this invention pertains to nucleic acid molecules encoding a GRP fusion protein which includes a nucleotide sequence encoding a first polypeptide having an amino acid sequence at least 80% (preferably at least 90%, or 95–99%) identical to an amino acid sequence shown in FIG. 3, (SEQ ID NO: 2) and a nucleic sequence encoding a second polypeptide corresponding to a moiety that facilitates detection or purification or alters the solubility of this fusion protein, such as glutathione-S-transferase, or an enzymatic activity such as alkaline phosphatase, or an epitope tag.

In another embodiment, the isolated nucleic acid molecule is a nucleotide sequence encoding a polypeptide fragment of at least about 15, 20, 25, 30, 40, 50, 60, 70, 100, 120, 140, 160, 180, 200, 220, 240, 260, 280, 300, 320, 350–399 amino acid residues in length, preferably at least about 100–300 amino acid residues in length, and more preferably at least about 140–260 amino acid residues in length corresponding to a protein having at least 80% the amino acid sequence shown in FIG. 3, (SEQ ID NO: 2). In a preferred embodiment, the polypeptide fragment has a GRP activity.

The GRP nucleic acid molecule can be non-coding, (e.g., probe, antisense or ribozyme molecules) or can encode a functional GRP polypeptide (e.g., a polypeptide which specifically modulates, e.g., by acting as either an agonist or antagonist, at least one biological activity of the GRP polypeptide). In a preferred embodiment, a GRP nucleic acid molecule includes the coding region of FIG. 1, (SEQ ID NO:1).

The invention also provides probes and primers composed of substantially purified oligonucleotides, which correspond to a region of nucleotide sequence which hybridizes to at least 6 consecutive nucleotides preferably at least 25 more preferably at least 40, 50 or at least 75 consecutive nucleotides of either sense or antisense sequences of FIG. 1, (SEQ ID NO: 1) or naturally occurring mutants thereof. In preferred embodiments, an oligonucleotide of the present invention specifically detects a GRP nucleic acid relative to other nucleic acid in a sample. In yet another embodiment, the probe/primer further includes a label which is capable of being detected.

Furthermore, in certain preferred embodiments, the subject GRP nucleic acids will include a transcriptional regulatory sequence, e.g., at least one of a transcriptional promoter or transcriptional enhancer sequence, which regulatory sequence is operably linked to the GRP gene sequences. Such regulatory sequences can be used to render the GRP gene sequences suitable for use as an expression vector. This invention also encompasses cells transfected with said expression vector whether prokaryotic or eukaryotic and a method for producing GRP proteins by employing the expression vectors.

Still another aspect of the invention pertains to isolated GRP proteins and active fragments thereof, such as polypeptides having an activity of a GRP polypeptide (e.g., at least one biological activity of GRP, such as the ability to bind, preferably with high affinity and specificity, a product of the lipid kinase phosphatidylinositol-3-OH kinase, such as PI-3, 4,5, or inositol 1,3,4,5—P4, or the ability to modulate integrin-mediated cell adhesion, or the ability to modulate membrane trafficking of cell surface receptors or a combination of such activities). The invention also provides an isolated preparation of a GRP protein. In a preferred embodiment, the isolated GRP protein comprises an amino acid sequence at least 85% identical to an amino acid sequence of FIG. 3, (SEQ ID NO: 2) and, preferably has an activity of GRP (e.g., at least one biological activity of GRP). Preferably, the protein is at least about 90%, more preferably at least about 91–95%, even more preferably at least about 96–98% and most preferably at least about 99% identical to the amino acid sequence of FIG. 3, (SEQ ID NO: 2).

In another embodiment, the GRP protein comprises an amino acid sequence of FIG. 3, (SEQ ID NO: 2). This invention also pertains to isolated polypeptides which include a PH domain having an amino acid sequence that is at least 85%, preferably at least 87%, more preferably at least 88, 89, 90, 91, 91, 92, 93, 94, 95, 96, 97, 98, 99% identical to a PH domain of an amino acid sequence shown in FIG. 3, (SEQ ID NO: 2) and a SEC7 domain having an amino acid sequence that is at least 85%, preferably at least 87%, more preferably at least 88, 89, 90, 91, 91, 92, 93, 94, 95, 96, 97, 98, 99% identical to a SEC7 domain of an amino acid sequence shown in FIG. 3, (SEQ ID NO: 2).

The invention also provides for a GRP fusion protein comprising a first polypeptide having an amino acid sequence at least 80% (preferably at least 90%, or 95–99%) identical to an amino acid sequence shown in FIG. 3, (SEQ ID NO: 2) and a nucleic sequence encoding a second polypeptide corresponding to a moiety that facilitates detection or purification or alters the solubility of the fusion protein, such as glutathione-S-transferase, or an enzymatic activity such as alkaline phosphatase, or an epitope tag. In preferred embodiments, the fusion protein include a PH domain of a GRP polypeptide. In yet another embodiment, the fusion protein comprises a SEC7 domain of a GRP polypeptide.

Polypeptides comprising a fragment of at least about 15, 20, 25, 30, 40, 50, 60, 70, 100, 120, 140, 160, 180, 200, 220, 240, 260, 280, 300, 320, 350–399 amino acid residues in length, preferably at least about 100–300 amino acid residues in length, and more preferably at least about 140–260 amino acid residues in length and having at least 80%, preferably at least 85%, more preferably at least 87, 88, 89, 90, 91, 91, 92, 93, 94, 95, 96, 97, 98, 99% identity with the amino acid sequence shown in FIGS. 1 and 3, SEQ ID NO: 2. In a preferred embodiment, the polypeptide fragment has a GRP activity.

Yet another aspect of the present invention features an immunogen comprising a GRP polypeptide in an immunogenic preparation, the immunogen being capable of eliciting an immune response specific for a GRP polypeptide; e.g. a humoral response, e.g. an antibody response; e.g. a cellular response. In preferred embodiments, the immunogen includes an antigenic determinant, e.g. a unique determinant, from a protein having at least 80%, preferably at least 85%, more preferably at least 87, 88, 89, 90, 91, 91, 92, 93, 94, 95, 96, 97, 98, 99% identity with the amino acid sequence represented by one of FIGS. 1 and 3, SEQ ID No: 2.

A still further aspect of the present invention features antibodies and antibody preparations specifically reactive with an epitope of the GRP immunogen.

The invention also features transgenic non-human animals, e.g. mice, rats, rabbits, chickens, frogs or pigs, having a transgene, e.g., animals which include (and preferably express) a heterologous form of a GRP gene described herein, or which misexpress an endogenous GRP gene, e.g., an animal in which expression of one or more of the subject GRP proteins is disrupted. Such a transgenic animal can serve as an animal model for studying cellular and tissue disorders comprising mutated or mis-expressed GRP alleles or for use in drug screening.

The invention also provides a probe/primer comprising a substantially purified oligonucleotide, wherein the oligonucleotide comprises a region of nucleotide sequence which hybridizes under stringent conditions to at least 12 consecutive nucleotides of sense or antisense sequences of any one or more of (SEQ ID NO: 1), or naturally occurring mutants thereof. In preferred embodiments, the probe/primer further includes a label group attached thereto and capable of being detected. The label group can be selected, e.g., from a group consisting of radioisotopes, fluorescent compounds, enzymes, and enzyme co-factors. Probes of the invention can be used as a part of a diagnostic test kit for identifying dysfunctions associated with mis-expression of a GRP protein, such as for detecting in a sample of cells isolated from a patient, a level of a nucleic acid encoding a GRP protein; e.g. measuring a GRP mRNA level in a cell, or determining whether a genomic GRP gene has been mutated or deleted. These so-called "probes/primers" of the invention can also be used as a part of "antisense" therapy which refers to administration or in situ generation of oligonucleotide probes or their derivatives which specifically hybridize (e.g. bind) under cellular conditions, with the cellular mRNA and/or genomic DNA encoding one or more of the subject GRP proteins so as to inhibit expression of that protein, e.g. by inhibiting transcription and/or translation. Preferably, the oligonucleotide is at least 12 nucleotides in length, although primers of 25, 40, 50, or 75 nucleotides in length are also encompassed.

Yet another aspect of the present invention concerns a method for modulating one or more of cell adhesion, membrane trafficking, insulin action on glucose transport of a cell by modulating a GRP biological activity, e.g., by potentiating or disrupting certain protein—protein interactions. In general, whether carried out in vivo, in vitro, or in situ, the method includes treating the cell with an effective amount of a GRP agent so as to alter, relative to the cell in the absence of treatment, at least one or more of (i) cell adhesion, (ii) membrane trafficking, or (iii) insulin action on glucose transport of a cell. Accordingly, the method can be carried out with GRP agents such as peptide and peptidomimetics or other molecules identified in the drug screens devised herein which agonize or antagonize the effects of signaling from a GRP protein or ligand binding of a GRP protein, e.g., an intracellular target molecule, e.g., an integrin molecule, or PI-3,4,5. Other GRP agents include antisense constructs for inhibiting expression of GRP proteins, and different domains of the GRP proteins that may act as dominant negative mutants of GRP proteins which competitively inhibit ligand interactions upstream and signal transduction downstream of a GRP protein.

In one embodiment, the subject method of modulating a GRP biological activity can be used in the treatment of lymphoid cells, e.g., T cells, natural killer cells, so as to modulate immune reactions such as graft rejection, autoimmunity, inflammation and homing of lymphocytes to inflamed areas. In another embodiment, the subject method is used to modulate metastasis, in which cancer cells are treated with an agent that modulates a GRP biological activity. In still another embodiment, the subject method can be used to modulate GRP biological activity in an insulin-responsive cell, e.g., adipocyte or a muscle cell. For instance, the present method can be used to regulate the glucose transporter translocation that underlies the mechanism of insulin action to stimulate glucose uptake into cells.

Another aspect of the invention relates to methods of modulating the attachment of a cell to a substrate, wherein the method comprises the steps of contacting a GRP-expressing cell with an agent that modulates the activity or the expression of a GRP protein, for example by modulating the interaction between GRP and an integrin molecule, then contacting said cell with a substrate containing an integrin ligand, e.g., an extracellular matrix protein, e.g., collagen, laminin, fibronectin, or am integral membrane protein mediating cell-cell adhesion, e.g., an ICAM family member. Use of this method is encompassed in skin grafting.

In yet another aspect, the invention provides a drug screening assay for screening test compounds for modulators, e.g., inhibitors, or alternatively, potentiators, of an interaction between a PI(3)kinase product, e.g., PI-3,4,5 and a GRP polypeptide receptor or a biologically active portion thereof, e.g., a PH domain. An exemplary method includes the following (a) forming a reaction mixture including: (i) a PI(3) kinase product, (ii) a GRP or PH domain polypeptide, and (iii) a test compound; and (b) detecting interaction of the PI(3) kinase product and GRP or PH polypeptides. A statistically significant change (potentiation or inhibition) in the interaction of the PI(3) kinase product and GRP or PH polypeptides in the presence of the test compound, relative to the interaction in the absence of the test compound, indicates a potential agonist (mimetic or potentiator) or antagonist (inhibitor) of said interaction. The reaction mixture can be a cell-free protein preparation, e.g., a reconstituted protein mixture or a cell lysate, or it can be a recombinant cell including a heterologous nucleic acid recombinantly expressing the GRP polypeptide.

In another embodiment, an assay is provided for screening for modulators of an interaction between a GRP polypeptide or biologically active portions thereof, e.g., SEC7 domain or PH domain, with signaling molecules. As an illustrative embodiment, test compounds that modulate the interaction between a GRP polypeptide or a SEC7 domain and an integrin adhesion receptor can be tested.

In preferred embodiments, the steps of the assay are repeated for a variegated library of at least 100 different test compounds, more preferably at least $10^3$, $10^4$ or $10^5$ different test compounds. The test compound can be, e.g., a peptide, a nucleic acid, a small organic molecule, or natural product extract (or fraction thereof).

Another aspect of the present invention provides a method of determining if a subject, e.g. an animal patient, is at risk for a disorder characterized by unwanted biological activity of a GRP polypeptide. The method includes detecting, in a tissue of the subject, the presence or absence of a genetic lesion characterized by at least one of (i) a mutation of a gene encoding a GRP protein; or (ii) the mis-expression of a GRP gene. In preferred embodiments, detecting the genetic lesion includes ascertaining the existence of at least one of: a deletion of one or more nucleotides from a GRP gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble GRP protein.

For example, detecting the genetic lesion can include (i) providing a probe/primer including an oligonucleotide containing a region of nucleotide sequence which hybridizes to a sense or antisense sequence of a GRP gene or naturally occurring mutants thereof, or 5' or 3' flanking sequences naturally associated with the GRP gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the GRP gene and, optionally, of the flanking nucleic acid sequences. For instance, the probe/primer can be employed in a polymerase chain reaction (PCR) or in a ligation chain reaction (LCR). In alternate embodiments, the level of a GRP protein is detected in an immunoassay using an antibody which is specifically immunoreactive with the GRP protein.

In another aspect, this invention features a method of cloning phospholipid binding proteins using labeled phospholipids, e.g., phosphatidylinositol as probes to screen expression libraries. In preferred embodiments, the probe includes a detectable label group attached thereto. The label group can be selected from, for example, the following radioisotopes, fluorescent compounds, enzymes, and enzyme co-factors.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIG. 1 is the complete cDNA sequence encoding full length mouse GRP (SEQ ID NO: 1) aligned with its predicted full length amino acid sequence (SEQ ID NO: 2).

Figure 4A:
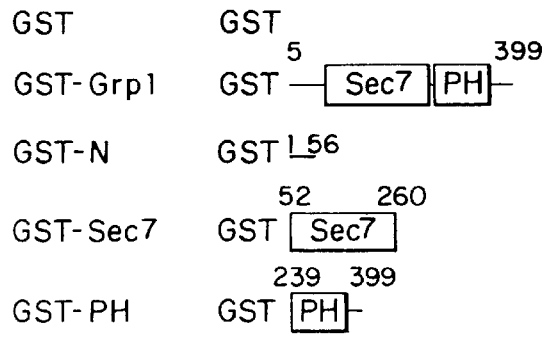
Figure 4B:
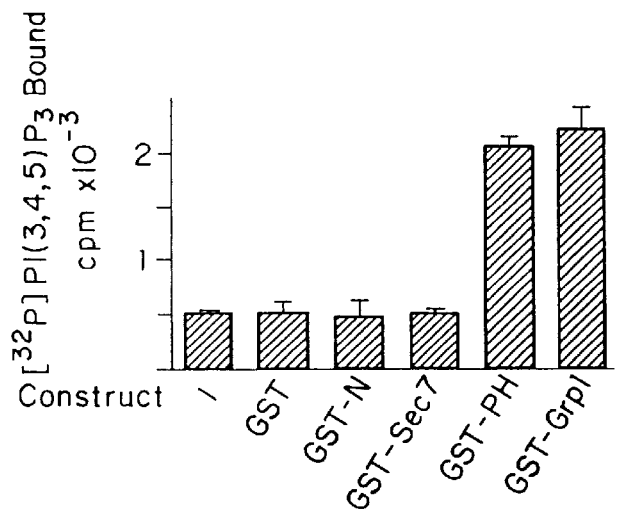

FIG. 4 shows the localization of PI(3,4,5)P$_3$ binding to the PH domain of GRP. (A) Schematic representation of fusion proteins of gluthathione-S-transferase (GST) and different parts of GRP. The numbers refer to the first and last amino acid of GRP included in the constructs. (B) Identification of the binding domain for PI(3,4,5)P$_3$ in GRP. (C) Binding specificity of the PH domain of GRP.

Figure 5A:
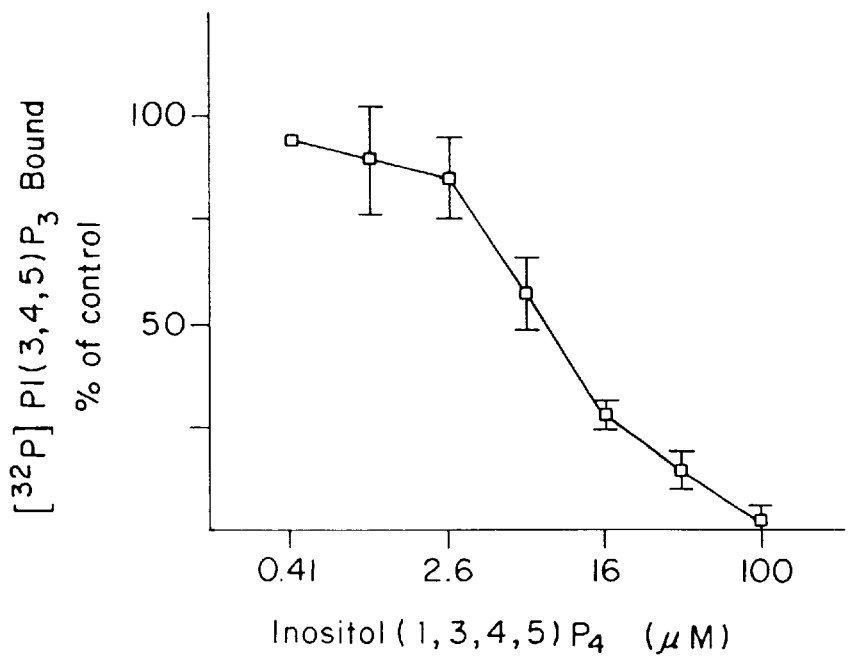
Figure 5B:
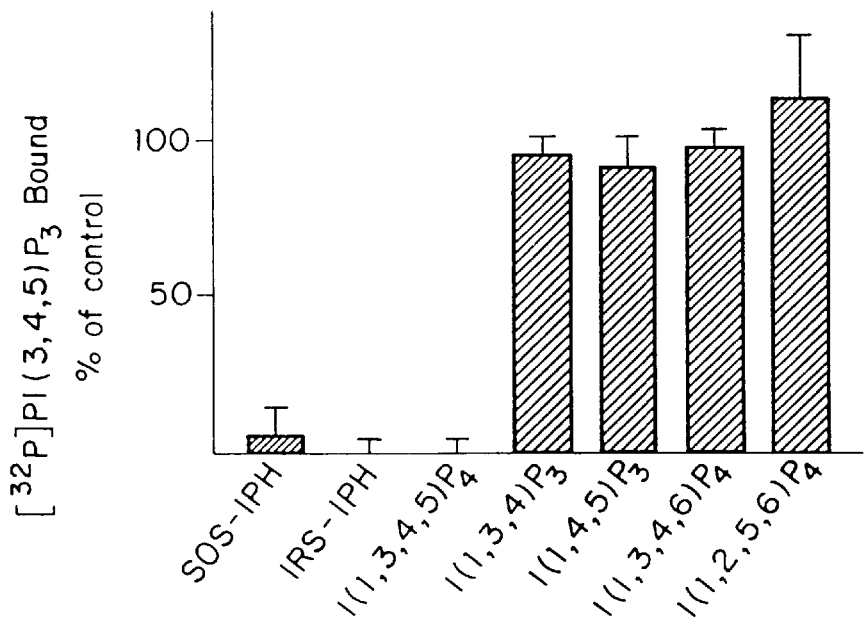

FIG. 5 shows the specificity of the GRP PH domain for binding of [$^{32}$P]PI(3,4,5)P$_3$ with respect to competition by the inositol phosphate head group of the phosphoinositides using GST-PH. (A) [$^{32}$P]PI(3,4,5)P$_3$ was incubated with varying concentrations of inositol (I)(3,4,5)P$_4$ and bound radioactivity determined. (B) Specificity of [$^{32}$P]PI(3,4,5)P$_3$ binding to the PH domains of GRP relative to the binding to GST fusion proteins containing amino acids 462–569 of murine Sos or amino acid 13–115 of murine IRS-1. (C) Comparisons of the deduced amino acid sequences of the PH domains of murine GRP SEQ ID NO: 5, B2-1/cytohesin-1 SEQ ID NO:6, Sos-1 SEQ ID NO:7, and IRS-1 SEQ ID NO:8. The basic motifs in the N terminal parts of the GRP and B2-1/cytohesin-1 molecules are outlined with heavy boxes and with asterisks. Light boxes delineate amino acid identity among the PH domains.

Figure 6:
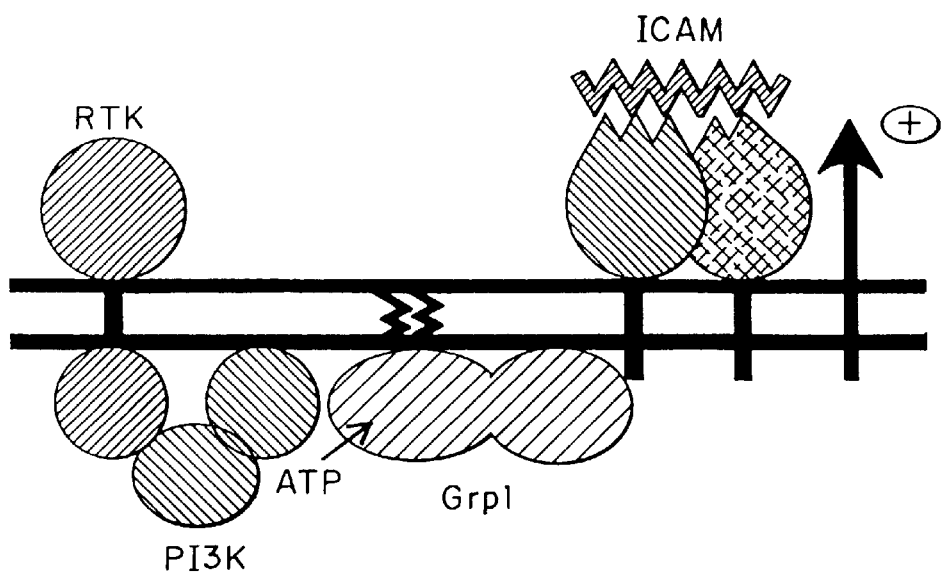

FIG. 6 is a schematic representation of a model summarizing the mechanism of GRP polypeptides as adaptors in modulating cell adhesion. According to this model, receptor tyrosine kinases (RTK) activate PI-3kinase (PI3k) such as p85/p110 type P-3 kinases to tyrosine phosphate sites. This leads to increased PI (3, 4, 5) P$_3$ at the plasma membrane which in turn binds to the PH domain of GRP. Membrane bound GRPs interact through their SEC7 homology regions to function as integrin β2 regulators. Cell adhesion is enhanced through GRP-mediated increased affinity of the integrin receptors for their ligands (ICAMs).

DETAILED DESCRIPTION OF THE INVENTION

The invention pertains to novel phosphatidylinositide binding proteins, referred to herein as "general receptors for phosphoinositide" or "GRPs", or active portions thereof which are capable of binding, preferably with high affinity and specificity to 3-phosphoinositides such as phosphatidyl inositol-3,4,5 and are capable of functioning as adaptors between membrane signaling and multiple downstream events such as cell adhesion and membrane trafficking. These GRP polypeptides preferably bind 3-phosphoinositides via a unique domain termed pleckstrin homology (PH) domain and are capable of enhancing the affinity of a cell to its substratum by binding to the cytoplasmic residues of integrin receptors, thereby increasing the affinity of the integrin molecule to a ligand such as an extracellular matrix protein (e.g., collagens, laminin, fibronectin) or to an integral membrane protein of the immunoglobulin superfamily (e.g., ICAM, VCAM, NCAM). Preferably, GRP polypeptides bind 3-phosphoinositides and are capable of stimulating membrane trafficking across a cell membrane such as, for example, by intracellular translocation of a protein from the Golgi apparatus to the cell membrane. In one embodiment, the GRP polypeptide is capable of regulating membrane trafficking of a cell surface protein, such as a glucose transporter, in an insulin-sensitive cell such as an adipocyte or a muscle cell. In another embodiment, the GRP polypeptide is a human GRP polypeptide which is expressed on a variety of cells including adipocytes, muscle, lymphoid, cancer and platelet cells.

One aspect of the invention pertains to GRP polypeptides which include a pleckstrin homology (PH) domain. As used herein, a PH domain is a protein module of approximately 100 amino acids typically located at the carboxy-terminal of proteins involved in signal transduction processes (See also Haslam et al. (1993) supra; Mayer et al. (1993) supra; Musacchio et al. (1993) TIBS 28:343–348). Typically, PH domains are very divergent and do not occupy a specific positions in molecules; alignments of PH domains show six conserved blocks which all contain several conserved hydrophobic residues which are thought to form a folded structure comprising seven to eight β-strands, most likely in one or two β-sheets, and a single helix (Musacchio et al. supra). PH domains have been identified in kinases and also in Vav, Dbl, Bcr, yeast cdc24, Ras-GAP, DM GAP, Ras-GRF, Sos PH, protein kinase C α, phospholipase C-δ1 (Burgering, B. M. T. and P. J. Coffer (1995) supra; Franke et al. (1995) supra; Coffer, P. J. and J. R. Woodgett (1991) supra), the serine/threonine kinase known variously as protein kinase B, Akt and Rac among others. The PH domain of β adrenergic receptor kinase may be involved in binding to G protein βγ complexes (Koch et al. (1993) J. Biol. Chem. 268:8256–8260). PH domains have been implicated in the binding to membranes containing PI 4,5-bisphosphate (Lemmon et al. (1995) supra), as well as to the binding of several proteins βγ subunits (Gβγ) of heterotrimeric G proteins (Touhara et al. (1994) supra; Satoshi et al. (1994) supra; Lemmon et al. (1995) supra), protein kinase C (17), WD motifs (18). In addition, the isolated PH domain of PLCg1 has been shown to specifically interact with high affinity with PI-4,5 P2 and D-myo-inositol 1,4,5 trisphosphate (Ins(1,4,5) P3) (Lemmon et al. (1995) supra).

Another aspect of the invention pertains to GRP polypeptides which include a SEC7 domain. SEC7 domains are presumably involved in membrane trafficking from the Golgi apparatus, as well as in the induction of cell adhesion through the enhanced β-integrin-dependent binding of lymphoid cells to extracellular molecules such as ICAM-1. A SEC7 domain was identified in yeast as part of a large protein containing 2008 amino acids. This protein was found to regulate glycoprotein secretion from the Golgi apparatus as evidenced by mutations of SEC7 resulting in the accumulation of glycoproteins within the Golgi apparatus and the exaggeration of Golgi cisternae (Achstetter et al. (1988) supra). The yeast SEC7 protein contains an unusual, highly charged acidic domain of 125 amino acids with 29% glutamate, 18% aspartate, and 21% serine. Within this region, stretches of 14 consecutive glutamate residues and 13 consecutive glutamates/aspartates are predicted. This domain is presumed to serve a structural role to interact with lipids or proteins on the cytoplasmic surface of the Golgi apparatus. The structural similarities between GRP and the yeast SEC7 protein indicate that GRP plays a role in glycoprotein processing by presumably interacting with lipids or proteins on the cytoplasmic surface of the Golgi apparatus. The finding that the GRP protein of the present invention contains a PH domain capable of binding to 3-phosphinositide and a SEC7 domain which, at least based on the yeast system, is involved in glycoprotein processing, provides a direct link between PI(3) kinase signaling and glycoprotein processing.

In a preferred embodiment of the invention, a GRP polypeptide having both a PH domain and a SEC7 domain is featured. This GRP polypeptide may function to convey information from the cell interior to the exterior via a mechanism termed "inside out signaling". In the immune system, inside out signaling has been associated with the orderly attachment of cells to their surrounding matrix, the adhesion of platelets to fibrinogen, the coupling of lymphocytes to their antigen presenting cells, and the phagocytosis of complement-opsonized targets by myelomonocytic phagocytes (reviewed by Diamond, M. S. and T. A. Springer (1993) supra; Hynes (1992) supra; and Sastry, S. K. and A. F. Horwitz (1993) supra).

The GRP polypeptides which include a PH domain of the present invention have been shown for the first time to bind with high affinity and specificity 3-phosphoinositides such as phosphatidyl inositol-3,4,5 (PI-3,4,5). In a preferred embodiment, GRP polypeptide binds 3-phosphoinositides but does not bind PI(3)P and PI(3,4)P2. As used herein, the term "3-phosphoinositide" refers generally to phosphatidylinositol (PI) molecules or hydrolyzed derivatives thereof having a phosphorylated hydroxyl group at position 3 of the myo-inositol ring. PIs are esters of a cyclic derivative of glucose having a phosphodiesterified fatty acid chain such as 1-stearoyl-2-arachidonyl species (18:0)(20:4) (reviewed in Fisher et al. (1984) *Trends in Biochem Sci* 9:53–56). PI is phosphodieterified at the D-1 position of the myo-inositol and has no phosphomonester substituents; PI-4 phosphate is phosphorylated at the D-4 position; whereas PI-4,5 is phosphorylated at the D4 and D5 positions. Thus, a preferred ligand of GRP polypeptides having a PH domain is PI-3,4,5 which is phosphorylated at the D3, D4 and D5 positions of the inositol ring. Also within the scope of the invention are hydrolyzed inositol derivatives of PI phosphorylated at the 3-position that bind selectively and with high affinity a GRP polypeptide. 3-phosphorylated inositol head groups selectively bind to GRP polypeptides, for example, GRP polypeptides bind to inositol 1,3,4,5-P4, but not to inositol 1,4,5 P3, inositol 1,3,4,6 P4 and inositol 1,2,5,6-P4. Previous work has shown PH domain binding to PI-4,5 P2 and Ins(1,4,5) P3, but not to 3-phosphoinositides, i.e., inositol groups having a phosphate group at position 3 of the inositol ring.

The mouse GRP protein is a modular intracellular protein of a calculated molecular weight of approximately 46–48 kDa having an amino acid sequence shown in FIGS. 1 and 3 (SEQ ID NO: 2). Each GRP polypeptide consists of an amino terminal portion of about 73 amino acids (about amino acids 1–73 of the sequence shown in FIGS. 1 and 3 (SEQ ID NO: 2) followed by a SEC7 domain of about 178 amino acids (about amino acids 74–252 of the sequence shown in FIGS. 1 and 3 (SEQ ID NO: 2), a PH domain of about 160 amino acids (about amino acids 258–384 of the sequence shown in FIGS. 1 and 3 (SEQ ID NO: 2), and a cytoplasmic tail of 14 amino acids (about amino acids 385–399 of the sequence shown in FIGS. 1 and 3 (SEQ ID NO: 2)).

GRP polypeptides having the ability to bind 3-phospoinositides with high affinity and specificity may be involved the mediating cellular signaling and membrane trafficking pathways, including membrane ruffling (1), chemotaxis (2), secretory responses (3), membrane trafficking of growth factor receptors (4), insulin secretion, cell regulated adhesion (5) and insulin-mediated translocation of glucose transporters to the cell surface. As used herein, the term "PI 3-kinase refers to isoforms of the p110 PI 3-Kinase, are capable of phosphorylating PI 4-phosphate and PI 4,5-bisphosphate at the 3-position. These enzymes apparently contribute to the regulated pools of PI 3,4-$P_2$ and PI-3,4,5$P_5$ stimulated by receptor or non-receptor tyrosine kinase activation (in the case of isoforms p110 and p110β) of G protein activation (in the case of p110). This term also includes a mammalian homolog of the yeast VPS34 protein (Herman, P. K. and D. Emris (1990) *Mol. Cell. Biol.* 10:6742–54), which can utilize only PI as substrate.

In addition, the GRP protein of the invention may be involved in integrin-mediated cell adhesion processes in the immune system, such as the orderly attachment of cells to their surrounding matrix, the adhesion of platelets to fibrinogen, the coupling of lymphocytes to their antigen presenting cells, and the phagocytosis of complement-opsonized targets by myelomonocytic phagocytes (reviewed by Diamond, M. S. and T. A. Springer (1993) supra; Hynes (1992) supra; and Sastry, S. K. and A. F. Horwitz (1993) supra). Accordingly, this invention emcompasses agents which modulate GRP activity to thereby modulate cell adhesion to the extracellular matrix and cell-cell interactions of a lymphoid cell. As such, the GRP polypeptides of the invention will be useful in modulating immune reactions such as graft rejection, autoimmunity, inflammation and homing of lymphocytes to inflammed areas.

The role of GRP polypeptides in integrin-mediated cell adhesion processes can be extended to other cell types. In a preferred embodiment, cell adhesion of a cancer cell, preferably, a metastatic cancer cell is encompassed, for example, by mediating cell migration, penetration through basement membranes and other molecular barriers. Accordingly, agents which modulate GRP activities can also be used for modulating cell adhesion to the extracellular matrix and cell-cell interactions of a metastatic cell.

Accordingly, this invention pertains to GRP polypeptides and to active portions thereof and to GRP polypeptides which include a PH domain or a SEC7 domain or both a PH domain and a SEC7 domain or a portion thereof. Such GRP polypeptides are referred to herein as polypeptides having an activity of GRP. The phrases "an activity of GRP", "having a GRP activity" or "GRP bioactivity" are used interchangeably herein to refer to molecules such as proteins and peptides which are capable of mimicking or antagonizing all or a portion of the biological/biochemical activities of a naturally occurring GRP protein. In addition, a polypeptide has bioactivity if it is a specific agonist or antagonist (competitor) of a mammalian GRP protein. In one embodiment, a protein having GRP bioactivity has high specificity and affinity binding to products of the lipid kinase PI(3) kinase, e.g., PI-3,4,5 and functions as an adaptor between receptor-mediated signaling and multiple downstream targets. In another embodiment, a protein having a GRP bioactivity modulates adhesion of a cell, e.g., a lymphoid cell, e.g., a T cell, a natural killer cell, so as to modulate immune reactions such as graft rejection, autoimmunity, inflammation and homing of lymphocytes to inflamed areas. In another embodiment, a protein having a GRP bioactivity modulates adhesion of a cancer cell during metastasis. In still another embodiment, a GRP protein modulates GRP bioactivity in an insulin-responsive cell, e.g., adipocyte or a muscle cell. For example, a GRP protein may regulate glucose transporter translocation that underlies insulin action in stimulating glucose uptake into cells. Other bioactivities of the subject GRP proteins are described herein or will be reasonably apparent to those skilled in the art.

In another embodiment, a portion of a GRP protein, e.g., a PH domain, may antagonize the biological/biochemical activities of a naturally occurring GRP protein by acting as a dominant negative regulator of a GRP protein or a fragment therof. In another embodiment, a portion of a GRP protein, e.g., a SEC7 domain, may activate, somewhat less efficiently, the biological/biochemical activities of a naturally occurring GRP protein.

Other aspects of the present invention relate to nucleic acids encoding GRP polypeptides, the GRP polypeptides themselves (including various fragments containing domains), antibodies immunoreactive with GRP proteins, and preparations of such compositions. Moreover, the present invention provides diagnostic and therapeutic assays and reagents for detecting and treating disorders involving, for example, aberrant expression (or loss thereof) of GRP, GRP interacting molecules (particularly PI-3,4-P and PI-3, 4,5), or signal transducers thereof.

In addition, drug discovery assays are provided for identifying agents which can modulate the biological function of GRP proteins, such as by altering the binding of GRP molecules to GRP interacting molecules (particularly PI-3, 4,5) or other intracellular targets (for example, integrins), or the ability of the bound GRP protein to transduce a signal. Such agents can be useful therapeutically to alter diseases dependent on cell adhesion and membrane trafficking.

Various aspects of the invention are described in further detail in the following subsections:

I. Nucleic Acids

As described below, one aspect of the invention pertains to isolated nucleic acids comprising nucleotide sequences encoding GRP polypeptides, and/or equivalents of such nucleic acids.

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject mammalian GRP polypeptides preferably includes no more than 10 kilobases (kb) of nucleic acid sequence which naturally immediately flanks the mammalian GRP gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "equivalent" is understood to include nucleotide sequences encoding functionally equivalent GRP polypeptides or functionally equivalent polypeptides having a GRP bioactivity refer to molecules such as proteins and peptides which are capable of mimicking or antagonizing all or a portion of the biological/biochemical activities of a GRP protein. In addition a polypeptide has bioactivity if it is a specific agonist or antagonist (competitor) of a naturally-occurring form of a mammalian GRP protein. In one embodiment a GRP protein of the present invention has a GRP bioactivity if it is exhibits high specificity and affinity binding to products of the lipid kinase PI(3) kinase, e.g., PI-3,4,5 and function as an adaptors between receptor-mediated signaling and multiple downstream targets. Equivalent nucleotide sequences will include sequences that differ by one or more nucleotide substitutions, additions or deletions, such as allelic variants; and will, therefore, include sequences that differ from the nucleotide sequence of the GRP gene shown in FIG. 1 (SEQ ID NO: 1) due to the degeneracy of the genetic code.

Other equivalents of GRP include structural equivalents. Structural equivalents preferably comprise an N-terminal region, a PH domain or portion thereof, a SEC 7 domain or portion thereof, and a short cytoplasmic tail. A portion of GRP polypeptide is at least about 15, 20, 25, 30, 40, 50, 60, 70, 100, 120, 140, 160, 180, 200, 220, 240, 260, 280, 300, 320, 350–399 amino acid residues in length, preferably at least about 100–300 amino acid residues in length, and more preferably at least about 140–260 amino acid residues in length corresponding to a protein having at least 80% the amino acid sequence shown in FIG. 3, (SEQ ID NO: 2). Preferred nucleotides of the present invention include nucleic acid molecules comprising a nucleotide sequence provided in FIG. 1 (SEQ. ID NO: 1), fragments thereof or equivalents thereof.

One embodiment the present invention features an isolated GRP nucleic acid molecule. In a preferred embodiment the GRP nucleic acid molecule of the present invention is isolated from a vertebrate organism. More preferred GRP nucleic acids are mammalian. Particularly preferred GRP nucleic acids are human or mouse.

A particularly preferred GRP nucleic acid is shown in SEQ ID NO: 1. The term GRP nucleic acid is also meant to include nucleic acic sequences which are homologous to the sequence shown in SEQ ID NO: 1 or a sequence which is complementary to that shown in SEQ ID NO: 1.

"Complementary" sequences as used herein refer to sequences which have sufficient complementarity to be able to hybridize, forming a stable duplex.

As used herein, the term "specifically hybridizes" refers to the ability of a nucleic acid probe/primer of the invention to hybridize to at least 15 consecutive nucleotides of a GRP gene, such as a GRP sequence designated in SEQ ID No: 1, or a sequence complementary thereto, or naturally occurring mutants thereof, such that it has less than 15%, preferably less than 10%, and more preferably less than 5% background hybridization to a cellular nucleic acid (e.g., mRNA or genomic DNA) encoding a protein other than a GRP protein, as defined herein.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the mammalian GRP sequences of the present invention.

The term "ortholog" refers to genes or proteins which are homologs via speciation, e.g., closely related and assumed to have common descent based on structural and functional considerations. Orthologous proteins function as recognizably the same activity in different species. The term "paralog" refers to genes or proteins which are homologs via gene duplication, e.g., duplicated variants of a gene within a genome. See also, Fritch, W M (1970) *Syst Zool* 19:99–113.

Thus, nucleic acids having a sequence that differs from the nucleotide sequences shown in SEQ ID No: 1 due to degeneracy in the genetic code are also within the scope of the invention. Such nucleic acids encode functionally equivalent peptides (i.e., a peptide having a biological activity of a mammalian GRP polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a mammalian GRP polypeptide. However, it is expected that DNA sequence polymorphisms that do lead to changes in the amino acid sequences of the subject GRP polypeptides will exist among mammalians. One skilled in the art will appreciate that these variations in one or more nucleotides (e.g., up to about 3–5% of the nucleotides) of the nucleic acids encoding polypeptides having an activity of a mammalian GRP polypeptide may exist among individuals of a given species due to natural allelic variation.

In a preferred embodiment a GRP nucleic acid is at least about 85% homologous to the nucleic acid sequence shown in FIG. 1 (SEQ ID NO:1) or its complement. In more preferred embodiments a GRP nucleic acid is at least about 90–99% homologous to the nucleic acid sequence shown in FIG. 1 (SEQ ID NO:1). In particularly preferred embodiments a GRP nucleic acid sequence is identical to the nucleotide sequence of FIG. 1 (SEQ ID No: 1).

In another embodiment a GRP nucleic acid includes a nucleic acid sequence at least 70% homologous to nucleotides 772–1150 of FIG. 1 (SEQ ID NO:1). In a preferred embodiment a GRP nucleic acid contains a sequence at least about 85% homologous to nucleotides 772–1150 of FIG. 1 (SEQ ID NO:1). In a more preferred embodiment a GRP nucleic acid of the present invention contains a nucleotide sequence at least about 90–99% homologous to nucleotides 772–1150 of FIG. 1 (SEQ ID NO:1). In a particularly preferred embodiment a GRP nucleic acid contains a sequence identical to the nucleotides 772–1150 of FIG. 1 (SEQ ID NO:1)

In another embodiment a GRP nucleic acid includes a nucleic acid sequence at least 80% homologous to nucleotides 217–754 of FIG. 1 (SEQ ID NO:1). In a preferred embodiment a GRP nucleic acid contains a sequence at least about 85% homologous to nucleotides 217–754 of FIG. 1 (SEQ ID NO:1). In a more preferred embodiment a GRP nucleic acid of the present invention contains a nucleotide sequence at least about 90% homologous to nucleotides 217–754 of FIG. 1 (SEQ ID NO:1). In a particularly preferred embodiment a GRP nucleic acid contains a sequence identical to the nucleotides 217–754 of FIG. 1 (SEQ ID NO:1).

In one embodiment a GRP nucleic acid contains a nucleotide sequence at least about 70% homologous to the sequence shown in nucleotides 772–1150 of FIG. 1 (SEQ. ID NO:1) and encodes a polypeptide with a GRP bioactivity. In a preferred embodiment a GRP nucleic acid contains a nucleotide sequence at least about 80% homologous to the sequence shown in nucleotides 772–1150 of FIG. 1 (SEQ. ID NO:1) and encodes a polypeptide with a GRP bioactivity. In a more preferred embodiment a GRP nucleic acid contains a nucleotide sequence at least about 90–99% homologous to the sequence shown in nucleotides 772–1150 of FIG. 1 (SEQ. ID NO:1) and encodes a polypeptide with a GRP bioactivity. In a particularly preferred a GRP nucleic acid contains a nucleotide sequence identical to the sequence shown in nucleotides 772–1150 of FIG. 1 (SEQ. ID NO:1) and encodes a polypeptide with a GRP bioactivity.

In one embodiment a GRP nucleic acid contains a nucleotide sequence at least about 70% homologous to the sequence shown in nucleotides 772–1150 of FIG. 1 (SEQ. ID NO:1) and encodes a polypeptide with a GRP bioactivity such as a polypeptide capable of binding to 3-phosphoroinositide. In a preferred embodiment a GRP nucleic acid contains a nucleotide sequence at least about 80% homologous to the sequence shown in nucleotides 772–1150 of FIG. 1 (SEQ. ID NO:1) and encodes a polypeptide with a GRP bioactivity. In a more preferred embodiment a GRP nucleic acid contains a nucleotide sequence at least about 90–99% homologous to the sequence shown in nucleotides 772–1150 of FIG. 1 (SEQ. ID NO:1) and encodes a polypeptide with a GRP bioactivity. In a particularly preferred embodiment a GRP nucleic acid contains a nucleotide sequence identical to the sequence shown in nucleotides 772–1150 of FIG. 1 (SEQ. ID NO:1) and encodes a polypeptide with a GRP bioactivity.

In a preferred embodiment a GRP nucleic acid is at least about 90% homologous to the coding sequence shown in FIG. 1 (SEQ ID NO:1) or its complement. In more preferred embodiments a GRP nucleic acid is at least about 96–97% homologous to the coding sequence shown in FIG. 1 (SEQ ID NO:1). In particularly preferred embodiments a GRP nucleic acid sequence is identical to the coding sequence of FIG. 1 (SEQ ID NO:1)

A GRP nucleic acid molecule can include an open reading frame encoding one of the mammalian GRP polypeptides of the present invention, including both exon and (optionally) intron sequences. A "recombinant gene" refers to nucleic acid encoding a mammalian GRP polypeptide and comprising mammalian GRP-encoding exon sequences, though it may optionally include intron sequences which are either derived from a chromosomal mammalian GRP gene or from an unrelated chromosomal gene. The term "intron" refers to a DNA sequence present in a given mammalian GRP gene which is not translated into protein and is generally found between exons.

In certain embodiments the subject GRP nucleic acid molecules include the 5' and 3' untranslated sequences which flank the gene, i.e., noncoding sequences, and do not encode for amino acids of a GRP polypeptide. In a preferred embodiment a GRP nuceleic acid molecule contains the coding region of SEQ ID NO:1.

"Transcriptional regulatory sequence" is a term used throughout the specification to refer to DNA sequences, such as initiation signals, enhancers, and promoters, which induce or control transcription of protein coding sequences with which they are operatively linked. In preferred embodiments, transcription of one of the recombinant mammalian GRP genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of GRP proteins.

Another aspect of the invention provides a nucleic acid which hybridizes under stringent conditions to a nucleic acid represented by FIG. 1 (SEQ ID No:1) or its complement. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a particularly preferred embodiment, a GRP nucleic acid of the present invention will bind to SEQ ID No: 1 under stringent conditions.

As used herein, the term "specifically hybridizes" or "specifically detects" refers to the ability of a nucleic acid molecule of the invention to hybridize to at least approximately 6, 12, 20, 30, 50, 100, 150, 200, or 300 consecutive nucleotides of a vertebrate, preferably mammalian, GRP gene, such as a GRP sequence designated in SEQ ID No:1, or a sequence complementary thereto, or naturally occurring mutants thereof, such that it shows more than 10 times more hybridization, preferably more than 100 times more hybridization, and even more preferably more than 100 times more hybridization than it does to a cellular nucleic acid (e.g., mRNA or genomic DNA) encoding a protein other than a vertebrate, preferably mammalian, GRP protein as defined herein. In a particularly preferred embodiment a GRP nucleic acid fragment specifically detects a GRP and not a B2-1/cytohesin, EST 01394 or cts18 nucleic acid.

In a further embodiment a GRP nucleic acid sequence encodes a vertebrate GRP polypeptide. Preferred nucleic acids of the present invention encode a GRP polypeptide which includes a polypeptide sequence corresponding to all or a portion of amino acid residues of SEQ ID No:2, e.g., at least 25, 50, 100, 150, 170, 190, 220, 240, 260, 280, 300, 320, 340, 360, 380 or 399 amino acid residues of that region. Genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "nucleic acid sequence encoding a vertebrate GRP polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same bioactivity.

In one embodiment a GRP nucleic acid encodes a polypeptide sequence at least 85% homologous to the sequence shown in SEQ ID NO: 2. In a preferred embodiment a GRP nucleic acid encodes a sequence at least 91–99% homologous to the sequence shown in SEQ ID NO: 2. In a more preferred embodiment a GRP nucleic acid encodes a sequence at least about 95% homologous to the sequence shown in SEQ ID NO: 2. In a particularly preferred embodiment the subject GRP nucleic acid molecule encodes the polypeptide shown in SEQ ID NO. 2.

In another embodiment, the subject GRP nucleic acids encode certain GRP domains. The PH domain (C-terminal amino acids 258–384) of the deduced GRP protein is 89–90% identical to the C-termini of previously described human GRP isoforms, including B2-1/cytohesin or cts18. In yet another embodiment, the subject GRP nucleic acids encode a SEC7 domain (amino acids 74–252) of the deduced GRP protein is 89–90% identical to the SEC7 of previously described human GRP isoforms, including B2-1/cytohesin or cts18.

In another embodiment a GRP nucleic acid encodes a polypeptide having a PH and SEC7 domain amino acid sequence at least 60% homologous to the amino acid shown in amino acids 258–384 and 74–252, respectively, of FIG. 1 (SEQ ID NO:2). In a preferred embodiment a GRP nucleic acid encodes a polypeptide with a PH or SEC7 domain amino acid sequence at least 70% homologous to the coding sequence shown in amino acids 258–384 and 74–252, respectively, of FIG. 1 (SEQ ID NO:2). In a more preferred embodiment a GRP nucleic acid encodes a polypeptide with a PH or SEC7 domain amino acid sequence at least 80% homologous to the PH or SEC7 domain sequence shown in amino acids 258–384 and 74–252, respectively, of SEQ ID NO: 2. In another preferred embodiment a GRP nucleic acid encodes a polypeptide with a PH or SEC7 domain amino acid sequence at least 90% homologous to the PH or SEC7 domain sequence shown in amino acids 258–384 and 74–252, respectively, of FIG. 1 (SEQ ID NO:2). In a particularly preferred embodiment a GRP nucleic acid encodes the PH or SEC7 domain shown in amino acids 258–384 and 74–252, respectively, of FIG. 1 (SEQ ID NO:2).

In another embodiment a GRP nucleic acid molecule encodes a polypeptide with a GRP bioactivity and contains PH domain and/or a SEC7 domain.

The subject GRP nucleic acid sequences allow for the generation of nucleic acid fragments (e.g., probes and primers) designed for use in identifying and/or cloning GRP homologs in other cell types, e.g. from other tissues, as well as GRP homologs from other mammalian organisms. For instance, the present invention also provides a nucleic acid fragment that can be used as a primer. The fragment can comprise a substantially purified oligonucleotide, containing a region of nucleotide sequence that hybridizes under stringent conditions to at least approximately 12, preferably 25, more preferably 40, 50 or 75 consecutive nucleotides of sense or anti-sense sequence of SEQ ID No:1, or naturally occurring mutants thereof. For instance, primers based on the nucleic acid represented in SEQ ID No:1 can be used in PCR reactions to clone GRP homologs.

In another embodiment, a GRP nucleic acid fragment is an oligonucleotide probe which specifically detects a GRP nucleic acid relative to a B2-1/cytohesin, EST 01394 or cts18 nucleic acid. In a preferred embodiment the subject oligonucleotide hybridizes under stringent conditions to at least 6 consecutive nucleotides encoding the GRP nucleic acid (SEQ ID NO:1).

In preferred embodiments, the probe further contains a label group and able to be detected, e.g. the label group can be a radioisotope, fluorescent compound, enzyme, or enzyme co-factor. Probes based on the subject GRP sequences can also be used to detect transcripts or genomic sequences encoding the same or homologous proteins.

As discussed in more detail below, the probes of the present invention can also be used as a part of a diagnostic test kit for identifying cells or tissue which misexpress a GRP protein, such as by measuring a level of a GRP-encoding nucleic acid in a sample of cells from a patient, e.g. detecting GRP mRNA levels or determining whether a genomic GRP gene has been mutated or deleted. Briefly, nucleotide probes can be generated from the subject GRP genes which facilitate histological screening of intact tissue and tissue samples for the presence (or absence) of GRP-encoding transcripts. Similar to the diagnostic uses of anti-GRP antibodies, the use of probes directed to GRP messages, or to genomic GRP sequences, can be used for both predictive and therapeutic evaluation of allelic mutations which might be manifest in certain disorders. Used in conjunction with immunoassays as described herein, the oligonucleotide probes can help facilitate the determination of the molecular basis for a disorder which may involve some abnormality associated with expression (or lack thereof) of a GRP protein. For instance, variation in polypeptide synthesis can be differentiated from a mutation in a coding sequence.

Another aspect of the invention relates to the use of isolated GRP nucleic acids in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject GRP proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a mammalian GRP protein. Alternatively, the antisense construct is an oligonucleotide probe which is generated ex vivo and which, when introduced into the cell causes inhibition of expression by hybridizing with the mRNA and/or genomic sequences of a mammalian GRP gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668.

Antisense approaches involve the design of oligonucleotides (either DNA or RNA) that are complementary to GRP mRNA. The antisense oligonucleotides will bind to the GRP mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a GRP gene could be used in an antisense approach to inhibit translation of endogenous GRP mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of GRP mRNA, antisense nucleic acids should be at least six nucleotides in length, and are preferably oligonucleotides ranging from 6 to about 50 nucleotides in length. In certain embodiments, the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or the blood-brain barrier (see, e.g., PCT Publication No. WO 89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

While antisense nucleotides complementary to the GRP coding region sequence could be used, those complementary to the transcribed untranslated region are most preferred.

The antisense molecules can be delivered to cells which express the GRP in vivo or in vitro. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

Since, it is often difficult to achieve intracellular concentrations of the antisense sufficient to suppress translation on endogenous mRNAs, a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous GRP transcripts and thereby prevent translation of the GRP mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Ribozyme molecules designed to catalytically cleave GRP mRNA transcripts can also be used to prevent translation of GRP mRNA and expression of GRP. (See, e.g., PCT International Publication WO90/11364, published Oct. 4, 1990; Sarver et al., 1990, Science 247:1222–1225). While ribozymes that cleave mRNA at site specific recognition sequences can be used to destroy GRP mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are numerous potential hammerhead ribozyme cleavage sites within the nucleotide sequence of human GRP cDNA. Preferably the ribozyme is engineered so that the cleavage recognition site is located near the 5' end of the GRP mRNA; i.e., to increase efficiency and minimize the intracellular accumulation of non-functional mRNA transcripts.

Ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in GRP.

As in the antisense approach, the ribozymes can be composed of modified oligonucleotides (e.g. for improved stability, targeting, etc.) and should be delivered to cells which express the GRP in vivo e.g., T cells. A preferred method of delivery involves using a DNA construct "encoding" the ribozyme under the control of a strong constitutive pol III or pol II promoter, so that transfected cells will produce sufficient quantities of the ribozyme to destroy endogenous GRP and inhibit translation. Because ribozymes unlike antisense molecules, are catalytic, a lower intracellular concentration is required for efficiency.

Endogenous GRP gene expression can also be reduced by inactivating or "knocking out" the GRP gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional GRP (or a completely unrelated DNA sequence) flanked by DNA homologous to the endogenous GRP gene (either the coding regions or regulatory regions of the GRP gene) can be used, with or without a selectable marker and/or a negative selectable marker, to transfect cells that express GRP in vivo. Insertion of the DNA construct, via targeted homologous recombination, results in inactivation of the GRP gene. Such approaches are particularly suited in the generation of animal offspring with an inactive GRP (e.g., see Thomas & Capecchi 1987 and Thompson 1989, supra). However this approach can be adapted for use in humans provided appropriate delivery means are used.

Alternatively, endogenous GRP gene expression can be reduced by targeting deoxyribonucleotide sequences complementary to the regulatory region of the GRP gene (i.e., the GRP promoter and/or enhancers) to form triple helical structures that prevent transcription of the GRP gene in target cells in the body. (See generally, Helene, C. 1991, Anticancer Drug Des., 6(6):569–84; Helene, C., et al., 1992, Ann, N.Y. Accad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

GRP nucleic acids can be obtained from mRNA present in any of a number of eukaryotic cells. It should also be possible to obtain nucleic acids encoding mammalian GRP polypeptides of the present invention from genomic DNA from both adults and embryos. For example, a gene encoding a GRP protein can be cloned from either a cDNA or a genomic library in accordance with protocols described herein, as well as those generally known to persons skilled in the art. Examples of tissues and/or libraries suitable for isolation of the subject nucleic acids include T cells, among others. A cDNA encoding a GRP protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a mammalian GRP protein can also be cloned using established polymerase chain reaction techniques in accordance with the nucleotide sequence information provided by the invention. The nucleic acid of the invention can be DNA or RNA. A preferred nucleic acid is a cDNA represented by a sequence shown in SEQ ID No:1.

Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Any of the subject nucleic acids can also be obtained by chemical synthesis. For example, nucleic acids of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448–7451), etc. Other techniques for chemically synthesizing oligodeoxyribonucleotides and oligoribonucleotides well known in the art such as for example solid phase phosphoramidite chemical synthesis.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

The subject nucleic acids may also contain modified bases. For example, a nucleic acid may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine,7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

A modified nucleic acid of the present invention may also include at least one modified sugar moiety selected from the group including but not limited to arabinose, 2-fluoroarabinose, xylulose, and hexose.

In yet another embodiment, the subject nucleic acid may include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

II. Recombinant Expression Vectors and Host Cells

The present invention also provides for vectors containing the subject nucleic acid molecules. As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions.

This invention also provides expression vectors containing a nucleic acid encoding a GRP polypeptide, operatively linked to at least one transcriptional regulatory sequence. "Operatively linked" is intended to mean that the nucleotide sequence is linked to a regulatory sequence in a manner which allows expression of the nucleotide sequence. Transcriptional regulatory sequences are art-recognized and are selected to direct expression of the subject mammalian GRP proteins. Exemplary regulatory sequences are described in Goeddel; Gene Expression Technology: Methods in Enzymology 185, Academic Press, San Diego, Calif. (1990).

In a preferred embodiment the expression vector of the present invention is capable of replicating in a cell. In one embodiment, the expression vector includes a recombinant gene encoding a peptide having GRP bioactivity. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject mammalian GRP proteins. Thus, another aspect of the invention features expression vectors for in vivo or in vitro transfection and expression of a mammalian GRP polypeptide in particular cell types so as to reconstitute the function of, or alternatively, abrogate the function of GRP in a tissue. For example, GRP or fragments thereof may be expressed in a cell in order to induce integrin-mediated attachment to an extracellular matrix and/or cell-cell adhesion in a cell to be transplanted into a subject. As an illustrative embodiment, transfected GRP may enhance the ability of a stem cell to engraft in bone marrow in replacement therapy. Alternatively, inhibition of the cell adhesion in a subject can be obtained by abrogate the function of GRP in therapeutic intervention in diseases as diverse as thrombosis, inflammation and cancer. In another embodiment, GRP or fragments thereof may be expressed in an insulin-sensitive cell to modulate membrane trafficking of glucose transporter.

In addition to viral transfer methods, such as those described above, non-viral methods can also be employed to cause expression of a subject GRP polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject GRP polypeptide gene by the targeted cell. Exemplary targeting means of this type include liposomal derived systems, poly-lysine conjugates, and artificial viral envelopes.

The recombinant GRP genes can be produced by ligating nucleic acid encoding a GRP protein, or a portion thereof, into a vector suitable for expression in either prokaryotic cells, eukaryotic cells, or both. Expression vectors for production of recombinant forms of the subject GRP polypeptides include plasmids and other vectors. For instance, suitable vectors for the expression of a GRP polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a GRP polypeptide is produced recombinantly utilizing an expression vector generated by sub-cloning the coding sequence of one of the GRP genes represented in SEQ ID No:1.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant GRP polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In some cases it will be desirable to express only a portion of a GRP protein. The subject vectors can also include fragments of a GRP nucleic acid encoding a fragment of a GRP protein. In a preferred embodiment, subdomains of a GRP protein are expressed. For example, a PH domain may be expressed in a cell to modulate the bioactivity of a GRP protein. A PH domain may act as a dominant negative regulator of the bioactivity of a GRP protein and thus inhibit cell adhesion, membrane trafficking.

The subject vectors can be used to transfect a host cell in order to express a recombinant form of the subject GRP polypeptides. The host cell may be any prokaryotic or eukaryotic cell. Thus, a nucleotide sequence derived from the cloning of mammalian GRP proteins, encoding all or a selected portion of the full-length protein, can be used to produce a recombinant form of a mammalian GRP polypeptide in a cell.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The present invention further pertains to methods of producing the subject GRP polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant GRP polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant GRP polypeptide is a fusion protein containing a domain which facilitates its purification, such as GST fusion protein or poly(His) fusion protein.

In other embodiments transgenic animals, described in more detail below could be used to produce recombinant proteins.

The present invention also provides for a recombinant transfection system, including a GRP gene construct operatively linked to a transcriptional regulatory sequence and a gene delivery composition for delivering the gene construct to a cell so that the cell expresses the GRP protein.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a mammalian GRP polypeptide or, in the case of anti-sense expression from the transferred gene, the expression of a naturally-occurring form of the GRP protein is disrupted.

A "delivery composition" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors).

III. Polypeptides

The present invention further pertains to isolated and/or recombinant forms of a GRP polypeptide. The terms "protein", "polypeptide" and "peptide" are used interchangably herein.

The term "recombinant protein" refers to a polypeptide of the present invention which is produced by recombinant DNA techniques, wherein generally, DNA encoding a mammalian GRP polypeptide is inserted into a suitable expression vector which is in turn used to transform a host cell to produce the heterologous protein. Moreover, the phrase "derived from", with respect to a recombinant GRP gene, is meant to include within the meaning of "recombinant protein" those proteins having an amino acid sequence of a native GRP γ protein, or a similar amino acid sequence which is generated by mutations including substitutions and deletions (including truncation) of a naturally occurring form of the protein.

The present invention also makes available isolated GRP polypeptides which are isolated from, or otherwise substantially free from other cellular proteins, especially other factors which may normally be associated with the GRP polypeptide. The term "substantially free of other cellular proteins" (also referred to herein as "contaminating proteins") or "substantially pure or purified preparations" are defined as encompassing preparations of GRP polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" are not meant to encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified GRP preparations will lack any contaminating proteins from the same animal from which GRP is normally produced, as can be accomplished by recombinant expression of, for example, a human GRP protein in a non-human cell.

In a particularly preferred embodiment a GRP protein includes the amino acid sequence shown in SEQ ID No:2. In particularly preferred embodiments, a GRP protein has a GRP bioactivity.

The present invention also provides for GRP proteins which have amino acid sequences evolutionarily related to the GRP proteins represented in SEQ ID No: 2. In a preferred embodiment, a GRP protein of the present invention is a mammalian GRP protein. The term "evolutionarily related to", with respect to amino acid sequences of mammalian GRP proteins, refers to both polypeptides having amino acid sequences which have arisen naturally, and also to mutational variants of mammalian GRP polypeptides which are derived, for example, by combinatorial mutagenesis. Such evolutionarily derived GRP polypeptides preferred by the present invention have a GRP bioactivity and are at least 90% homologous and most preferably at least 95% homologous with the amino acid sequence shown in SEQ ID No: 2.

In certain embodiments it will be advantageous to provide homologs of one of the subject GRP polypeptides which function in a limited capacity as one of either a GRP γ agonist (mimetic) or a GRP antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of GRP proteins.

Homologs of each of the subject GRP proteins can be generated by mutagenesis, such as by discrete point mutation(s), or by truncation. For instance, mutation can give rise to homologs which retain substantially the same, or merely a subset, of the biological activity of the GRP polypeptide from which it was derived. Alternatively, antagonistic forms of the protein can be generated which are able to inhibit the function of the naturally occurring form of the protein, such as by competitively binding to a downstream or upstream member of the GRP cascade which includes the GRP protein. In addition, agonistic forms of the protein may be generated which are constitutively active. Thus, the mammalian GRP protein and homologs thereof provided by the subject invention may be either positive or negative regulators of cell adhesion or membrane trafficking.

The recombinant GRP polypeptides of the present invention also include homologs of the wild type GRP proteins, such as versions of those protein which are resistant to proteolytic cleavage, as for example, due to mutations which alter ubiquitination or other enzymatic targeting associated with the protein.

GRP polypeptides may also be chemically modified to create GRP derivatives by forming covalent or aggregate conjugates with other chemical moieties, such as glycosyl groups, lipids, phosphate, acetyl groups and the like. Covalent derivatives of GRP proteins can be prepared by linking the chemical moieties to functional groups on amino acid sidechains of the protein or at the N-terminus or at the C-terminus of the polypeptide.

Modification of the structure of the subject mammalian GRP polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the GRP polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, WH Freeman and Co.: 1981). Whether a change in the amino acid sequence of a peptide results in a functional GRP homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

In another embodiment a GRP has a GRP bioactivity and is encoded by the nucleic acid shown in FIG. 1 (SEQ ID NO:1).

Full length proteins or fragments corresponding to one or more particular motifs and/or domains or to arbitrary sizes, for example, at least 25, 50, 75, 100, 125, 150, 175, 200, 225, 250, 275, 300–399 amino acids in length are within the scope of the present invention. For example, isolated GRP polypeptides can include all or a portion of an amino acid sequences corresponding to a GRP polypeptide represented in or homologous to FIG. 1 (SEQ ID NO:2). Isolated peptidyl portions of GRP proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a GRP polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") GRP protein.

In still a further embodiment an isolated or recombinant GRP polypeptide includes a sequence corresponding to a PH domain (258–384 of SEQ ID NO:2 and is at least 85%, more preferably about 90%, and most preferably at least about 91, 92, 93, 94, 95, 96, 97, 98, 99% identical to a PH domain of the amino acid sequence shown in FIG. 1 (SEQ ID NO:2).

In still a further embodiment an isolated or recombinant GRP polypeptide includes a sequence corresponding to a SEC7 domain (74–252 of SEQ ID NO:2 and is at least 85%, more preferably about 90%, and most preferably at least about 91, 92, 93, 94, 95, 96, 97, 98, 99% identical to a SEC7 domain of the amino acid sequence shown in FIG. 1 (SEQ ID NO:2).

In certain embodiments a GRP polypeptide has a GRP bioactivity and comprises a structurally and functionally modular protein having a PH domain or a SEC7 domain.

In certain preferred embodiments, the invention features a purified or recombinant GRP polypeptide having a molecular weight of approximately 46–48 kD. It will be understood that certain post-translational modifications can increase the apparent molecular weight of the GRP protein relative to the unmodified polypeptide chain.

This invention further provides a method for generating sets of combinatorial mutants of the subject GRP proteins as well as truncation mutants, and is especially useful for identifying potential variant sequences (e.g. homologs) that modulate a GRP bioactivity. The purpose of screening such combinatorial libraries is to generate, for example, novel GRP homologs which can act as either agonists or antagonist, or alternatively, possess novel activities all together. To illustrate, combinatorially-derived homologs can be generated to have an increased potency relative to a naturally occurring form of the protein.

Likewise, GRP homologs can be generated by the present combinatorial approach to selectively inhibit (antagonize) an authentic GRP. For instance, mutagenesis can provide GRP homologs which are able to bind other signal pathway proteins (or DNA) yet prevent propagation of the signal, e.g. the homologs can be dominant negative mutants. Moreover, manipulation of certain domains of GRP by the present method can provide domains more suitable for use in fusion proteins.

In one embodiment, the variegated library of GRP variants is generated by combinatorial mutagenesis at the nucleic acid level, and is encoded by a variegated gene library. For instance, a mixture of synthetic oligonucleotides can be enzymatically ligated into gene sequences such that the degenerate set of potential GRP sequences are expressible as individual polypeptides, or alternatively, as a set of larger fusion proteins (e.g. for phage display) containing the set of GRP sequences therein.

There are many ways by which such libraries of potential GRP homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential GRP sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for a GRP clone in order to generate a variegated population of GRP fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a GRP coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of GRP homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate GRP sequences created by combinatorial mutagenesis techniques.

In one embodiment, cell based assays can be exploited to analyze the variegated GRP library. For instance, the library of expression vectors can be transfected into a cell line ordinarily responsive to GRP. The transfected cells are then exposed to an extracellular signal and the effect of the GRP mutant can be detected, e.g. cell adhesion. Plasmid DNA can then be recovered from the cells which score for inhibition, or alternatively, potentiation of GRP activity, and the individual clones further characterized.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811–7815; Yourvan et al., 1992, Parallel Problem Solving from Nature, 2., In Maenner and Manderick, eds., Elsevir Publishing Co., Amsterdam, pp. 401–410; Delgrave et al., 1993, Protein Engineering 6(3):327–331).

The invention also provides for reduction of the mammalian GRP proteins to generate mimetics, e.g. peptide or non-peptide agents, which are able to disrupt binding of a mammalian GRP polypeptide of the present invention with binding proteins or interactors. Thus, such mutagenic techniques as described above are also useful to map the determinants of the GRP proteins which participate in protein-protein interactions involved in, for example, binding of the subject mammalian GRP polypeptide to proteins which may function upstream (including both activators and repressors of its activity) or to proteins or nucleic acids which may function downstream of the GRP polypeptide, whether they are positively or negatively regulated by it. To illustrate, the critical residues of a subject GRP polypeptide which are involved in molecular recognition of interactor proteins or molecules upstream or downstream of a GRP (such as, for example PH domains, SEC7 domains) can be determined and used to generate GRP -derived peptidomimetics which competitively inhibit binding of the authentic GRP protein to that moiety. By employing, for example, scanning mutagenesis to map the amino acid residues of each of the subject GRP proteins which are involved in binding other extracellular proteins, peptidomimetic compounds can be generated which mimic those residues of the GRP protein which facilitate the interaction. Such mimetics may then be used to interfere with the normal function of a GRP protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted γ lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Communl26:419; and Dann et al. (1986) Biochem Biophys Res Commun 134:71).

In another embodiment, the coding sequences for the polypeptide can be incorporated as a part of a fusion gene including a nucleotide sequence encoding a different polypeptide to generate a fusion protein or chimeric protein.

A "chimeric protein" or "fusion protein" is a fusion of a first amino acid sequence encoding one of the subject mammalian GRP polypeptides with a second amino acid sequence defining a domain (e.g. polypeptide portion) foreign to and not substantially homologous with any domain of one of the mammalian GRP proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-GRP-Y, wherein GRP represents a portion of the protein which is derived from one of the mammalian GRP proteins, and X and Y are independently absent or represent amino acid sequences which are not related to one of the mammalian GRP sequences in an organism, including naturally occurring mutants.

Fusion proteins can also facilitate the expression of proteins, and accordingly, can be used in the expression of the mammalian GRP polypeptides of the present invention. For example, GRP polypeptides can be generated as glutathione-S-transferase (GST-fusion) proteins. Such GST-fusion proteins can enable easy purification of the GRP polypeptide, as for example by the use of glutathione-derivatized matrices (see, for example, Current Protocols in Molecular Biology, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

In preferred embodiments, fusion proteins of the present invention contain a detectable label or a matrix binding domain.

The preparation of fusion proteins is often desirable when producing an immunogenic fragment of a GRP protein. For example, the VP6 capsid protein of rotavirus can be used as an immunologic carrier protein for portions of the GRP polypeptide, either in the monomeric form or in the form of a viral particle. The nucleic acid sequences corresponding to the portion of a subject GRP protein to which antibodies are to be raised can be incorporated into a fusion gene construct which includes coding sequences for a late vaccinia virus structural protein to produce a set of recombinant viruses expressing fusion proteins comprising GRP epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a GRP protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of a GRP polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of GRP proteins can also be expressed and presented by bacterial cells.

IV. Antibodies

Another aspect of the invention pertains to an antibody specifically reactive with a mammalian GRP protein. For example, by using immunogens derived from a GRP protein, e.g. based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a mammalian GRP polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a GRP protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a GRP protein of a mammal, e.g. antigenic determinants of a protein represented by FIG. 1 (SEQ ID NO:2).

Following immunization of an animal with an antigenic preparation of a GRP polypeptide, anti-GRP antisera can be obtained and, if desired, polyclonal anti-GRP antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256:495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a mammalian GRP polypeptide of the present invention and monoclonal antibodies isolated from a culture comprising such hybridoma cells.

The term antibody as used herein is intended to include fragments thereof which are also specifically reactive with one of the subject mammalian GRP polypeptides. Antibodies can be fragmented using conventional techniques and the fragments screened for utility in the same manner as described above for whole antibodies. For example, $F(ab)_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a GRP protein conferred by at least one CDR region of the antibody.

Antibodies which specifically bind GRP epitopes can also be used in immunohistochemical staining of tissue samples in order to evaluate the abundance and pattern of expression of each of the subject GRP polypeptides. Anti-GRP antibodies can be used diagnostically in immuno-precipitation and immuno-blotting to detect and evaluate GRP protein levels in tissue as part of a clinical testing procedure. Likewise, the ability to monitor GRP protein levels in an individual can allow determination of the efficacy of a given treatment regimen for an individual afflicted with such a disorder. Diagnostic assays using anti-GRP antibodies can include, for example, immunoassays designed to aid in early diagnosis of a degenerative disorder, particularly ones which are manifest at birth. Diagnostic assays using anti-GRP polypeptide antibodies can also include immunoassays designed to aid in early diagnosis and phenotyping neoplastic or hyperplastic disorders.

Another application of anti-GRP antibodies of the present invention is in the immunological screening of cDNA libraries constructed in expression vectors such as λ gt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a GRP protein, e.g. other orthologs of a particular GRP protein or other paralogs from the same species, can then be detected with antibodies, as, for example, reacting nitrocellulose filters lifted from infected plates with anti-GRP antibodies. Positive phage detected by this assay can then be isolated from the infected plate. Thus, the presence of GRP homologs can be detected and cloned from other animals, as can alternate isoforms (including splicing variants) from humans.

In certain embodiment, it will be desirable to attach a label group to the subject antibodies to facilitate detection. One means for labeling an anti-GRP protein specific antibody is via linkage to an enzyme and use in an enzyme immunoassay (EIA) (Voller, "The Enzyme Linked Immunosorbent Assay (ELISA)", Diagnostic Horizons 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) Enzyme Immunoassay, CRC Press, Boca Raton, Fla., 1980; Ishikawa, et al., (eds.) Enzyme Immunoassay, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

It is also possible to label the antibody with a fluorescent compound. When the fluorescently labeled antibody is exposed to light of the proper wave length, its presence can then be detected. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

V. Pharmaceutical Preparations

The subject modulating agents can be administered to a subject at therapeutically effective dose to treat or ameliorate a disorder benefiting from the modulation of GRP. The data obtained from cell culture assays and animal studies can be used in formulating a range of dosage for use in humans. The dosage of such compounds lies preferably within a range of circulating or tissue concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In clinical settings, the gene delivery systems for the therapeutic GRP gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A mammalian GRP gene, such as any one of the sequences represented in SEQ ID NO:1, or a sequence homologous thereto can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Pharmaceutical preparations for use in accordance with the present invention may also be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical preparations may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation, the preparations for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

The compositions may, if desired, be presented in a pack or dispenser device, or as a kit with instructions. The composition may contain one or more unit dosage forms containing the active ingredient. The pack may for example comprise metal or plastic foil, such as a blister pack. The pack or dispenser device may be accompanied by instructions for administration.

VI. Transgenic Animals

The present invention also provides for transgenic animals in which expression of a genomic sequence encoding a functional GRP polypeptide is enhanced, induced, disrupted, prevented or suppressed. The transgenic animals produced in accordance with the present invention will include exogenous genetic material. As set out above, the exogenous genetic material will, in certain embodiments, be a DNA sequence which results in the production of a GRP protein (either agonistic or antagonistic), and antisense transcript, or a GRP mutant. Further, in such embodiments the sequence will be attached to a transcriptional control element, e.g., a promoter, which preferably allows the expression of the transgene product in a specific type of cell.

As used herein, the term "transgene" means a nucleic acid sequence (whether encoding or antisense to one of the mammalian GRP polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the mammalian GRP proteins, e.g. either agonistic or antagonistic forms. However, transgenic animals in which the recombinant GRP gene is silent are also encompassed, as for example, the FLP or CRE recombinase dependent constructs described below. Moreover, "transgenic animal" also includes those recombinant animals in which gene disruption of one or more GRPγ genes is caused by human intervention, including both recombination and antisense techniques.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that one of the recombinant mammalian GRP genes is present and/or expressed or disrupted in some tissues but not others.

These systems may be used in a variety of applications. For example, the cell- and animal-based model systems may be used to further characterize GRP genes and proteins. In addition, such assays may be utilized as part of screening strategies designed to identify compounds which are capable of ameliorating disease symptoms. Thus, the animal- and cell-based models may be used to identify drugs, pharmaceuticals, therapies and interventions which may be effective in treating disease.

One aspect of the present invention concerns transgenic animals which are comprised of cells (of that animal) which contain a transgene of the present invention and which preferably (though optionally) express an exogenous GRP protein in one or more cells in the animal. A GRP transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a GRP protein can be essential for many forms of lineage analysis and can additionally provide a means to assess the effects of, for example, lack of GRP expression which might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject GRP proteins. For example, excision of a target sequence which interferes with the expression of a recombinant GRP gene, such as one which encodes an antagonistic homolog or an antisense transcript, can be designed to activate expression of that gene. This interference with expression of the protein can result from a variety of mechanisms, such as spatial separation of the GRP gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992)

PNAS 89:6232–6236; Orban et al. (1992) PNAS 89:6861–6865) or the FLP recombinase system of Saccharomyces cerevisiae (O'Gorman et al. (1991) Science 251:1351–1355; PCT publication WO 92/15694) can be used to generate in vivo site-specific genetic recombination systems.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant GRP protein can be regulated via control of recombinase expression.

Use of the cre/loxP recombinase system to regulate expression of a recombinant GRP protein requires the construction of a transgenic animal containing transgenes encoding both the Cre recombinase and the subject protein. Animals containing both the Cre recombinase and a recombinant GRP gene can be provided through the construction of "double" transgenic animals. A convenient method for providing such animals is to mate two transgenic animals each containing a transgene, e.g., a GRP gene and recombinase gene.

One advantage derived from initially constructing transgenic animals containing a GRP transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic GRP transgene is silent will allow the study of progeny from that founder in which disruption of GRP mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the GRP transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a GRP transgene could remain silent into adulthood until "turned on" by the introduction of the trans-activator.

In one embodiment, gene targeting, which is a method of using homologous recombination to modify an animal's genome, can be used to introduce changes into cultured embryonic stem cells. By targeting a GRP gene of interest e.g., in embryonic stem (ES) cells, these changes can be introduced into the germlines of animals to generate chimeras. The gene targeting procedure is accomplished by introducing into tissue culture cells a DNA targeting construct that includes a segment homologous to a target GRP locus, and which also includes an intended sequence modification to the GRP genomic sequence (e.g., insertion, deletion, point mutation). The treated cells are then screened for accurate targeting to identify and isolate those which have been properly targeted.

Methods of culturing cells and preparation of knock out constructs for insertion are known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) Current Topics in Devel. Biol. 20:357–371); and by Hogan et al. (Manipulating the Mouse Embryo: A Laboratory Manual, Cold Spring Harbor Laboratory Press, Cold Spring Harbor, N.Y. [1986]).

Introduction of the transgenic constructs nucleotide sequence into the embryo may be accomplished by any means known in the art such as, for example, microinjection, electroporation, calcium phosphate, or lipofection. Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264).

Other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a GRP-gene can be controlled by recombinase sequences.

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

Uses and Methods of the Invention

VI. Drug Screening Assays

The present invention also provides for assays which can be used to screen for compounds, including GRP homologs, which are either agonists or antagonists of the normal cellular function of the subject GRP polypeptides, or portions thereof such as PH domain or a SEC7 domain. Screened compounds, for example antagonists of GRP bioactivity, may be useful in treating many diseases dependent upon cell adhesion: e.g., immune reactions such as graft rejections, autoimmunity, potentially inflammation and homing of lymphocytes to inflamed areas; metastasis of cancer cells; cellular migration and invasion in atherosclerosis, among others. In still, another embodiment, the subject method can be used to modulate GRP bioactivity in an insulin-responsive cell, e.g., adipocyte or a muscle cell. For instance the present method can be used to regulate the glucose transporter translocation that underlies the mechanism of insulin action to stimulate glucose uptake into cells.

For example, inhibitors, or alternatively, potentiators, of an interaction between a PI-3-kinase product, e.g., PI-3,4-P and PI-3,4,5 and a GRP polypeptide receptor or a PH domain. A variety of assay formats can be used for the subject assays. An exemplary method includes the steps of (a) forming a reaction mixture including: (i) a PI'3 kinase product, (ii) a GRP or PH domain polypeptide, and (iii) a test compound; and (b) detecting interaction of the PI'3 kinase product and GRP or PH polypeptides. A statistically significant change (potentiation or inhibition) in the interaction of the PI'3 kinase product and GRP or PH polypeptides in the presence of the test compound, relative to the interaction in the absence of the test compound, indicates a potential agonist (mimetic or potentiator) or antagonist (inhibitor) of said interaction. The reaction mixture can be a cell-free protein preparation, e.g., a reconsistuted protein mixture or a cell lysate, or it can be a recombinant cell including a heterologous nucleic acid recombinantly expressing the GRP polypeptide.

In one embodiment, an assay is provided for screening for modulators of an interaction between a GRP polypeptide or various domains thereof, e.g., SEC7 domain or PH domain, with signaling molecules. As an illustrative embodiment, test compounds that modulate the interaction between a GRP polypeptide or a SEC7 domain and an integrin adhesion receptor can be tested.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements.

In an exemplary screening assay of the present invention, the compound of interest is contacted with proteins which may function upstream (including both activators and repressors of its activity) or to proteins or nucleic acids which may function downstream of the GRP polypeptide, whether they are positively or negatively regulated by it. To the mixture of the compound and the upstream or downstream element is then added a composition containing a GRP polypeptide. Detection and quantification of the interaction of GRP with its upstream or downstream elements provide a means for determining a compound's efficacy at inhibiting (or potentiating) complex formation between GRP and the GRP-binding elements. The term "interact" as used herein is meant to include detectable interactions between molecules, such as can be detected using, for example, a yeast two hybrid assay. The term interact is also meant to include "binding" interactions between molecules. Interactions may be protein-protein or protein-nucleic acid in nature.

The efficacy of the compound can be assessed by generating dose response curves from data obtained using various concentrations of the test compound. Moreover, a control assay can also be performed to provide a baseline for comparison. In the control assay, isolated and purified GRP polypeptide is added to a composition containing the GRP-binding element, and the formation of a complex is quantitated in the absence of the test compound.

Complex formation between the GRP polypeptide and a GRP binding element may be detected by a variety of techniques. Modulation of the formation of complexes can be quantitated using, for example, detectably labeled proteins such as radiolabeled, fluorescently labeled, or enzymatically labeled GRP polypeptides, by immunoassay, or by chromatographic detection.

Typically, it will be desirable to immobilize either GRP or its binding protein to facilitate separation of complexes from uncomplexed forms of one or both of the proteins, as well as to accommodate automation of the assay. Binding of GRP to an upstream or downstream element, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/GRP (GST/GRP) fusion proteins can be adsorbed onto glutathione sepharose beads (Sigma Chemical, St. Louis, Mo.) or glutathione derivatized microtitre plates, which are then combined with the cell lysates, e.g. an 35S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of GRP-binding protein found in the bead fraction quantitated from the gel using standard electrophoretic techniques such as described in the appended examples.

Other techniques for immobilizing proteins on matrices are also available for use in the subject assay. For instance, either GRP or its cognate binding protein can be immobilized utilizing conjugation of biotin and streptavidin. For instance, biotinylated GRP molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with GRP but which do not interfere with binding of upstream or downstream elements can be derivatized to the wells of the plate, and GRP trapped in the wells by antibody conjugation. As above, preparations of a GRP-binding protein and a test compound are incubated in the GRP-presenting wells of the plate, and the amount of complex trapped in the well can be quantitated. Exemplary methods for detecting such complexes, in addition to those described above for the GST-immobilized complexes, include immunodetection of complexes using antibodies reactive with the GRP binding element, or which are reactive with GRP protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the GRP-BP. To illustrate, the GRP-BP can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2, 4-dinitrobenzene (Habig et al (1974) J Biol Chem 249:7130).

For processes which rely on immunodetection for quantitating one of the proteins trapped in the complex, antibodies against the protein, such as anti-GRP antibodies, can be used. Alternatively, the protein to be detected in the complex can be "epitope tagged" in the form of a fusion protein which includes, in addition to the GRP sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

In addition to cell-free assays, such as described above, the readily available source of mammalian GRP proteins provided by the present invention also facilitates the generation of cell-based assays for identifying small molecule agonists/antagonists and the like. For example, cells can be caused to overexpress a recombinant GRP protein in the presence and absence of a test compound of interest, with the assay scoring for modulation in GRP responses by the target cell mediated by the test agent. As with the cell-free assays, compounds which produce a statistically significant change in GRP-dependent responses (either inhibition or potentiation) can be identified. In an illustrative embodiment, the expression or activity of a GRP is modulated embryos or cells and the effects of compounds of interest on the readout of interest (such as apoptosis) are measured. For example, the expression of genes which are up- or down-regulated in response to a GRP-dependent signal cascade can be assayed. In preferred embodiments, the regulatory regions of such genes, e.g., the 5' flanking promoter and enhancer regions, are operatively linked to a marker (such as luciferase) which encodes a gene product that can be readily detected.

Monitoring the influence of compounds on cells may be applied not only in basic drug screening, but also in clinical trials. In such clinical trials, the expression of a panel of genes may be used as a "read out" of a particular drug's therapeutic effect.

In another aspect of the invention, the subject GRP polypeptides can be used to generate a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with GRP ("GRP-binding proteins" or "GRP-bp". Such GRP-binding proteins would likely regulators of GRP bioactivity.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a GRP polypeptide. The second hybrid protein encodes a transcriptional activation domain fused in frame to a sample gene from a cDNA library. If the bait and sample hybrid proteins are able to interact, e.g., form a GRP-dependent complex, they bring into close proximity the two domains of the transcriptional activator. This proximity is sufficient to cause transcription of a reporter gene which is operatively linked to a transcriptional regulatory site responsive to the transcriptional activator, and expression of the reporter gene can be detected and used to score for the interaction of the GRP and sample proteins.

VI. Diagnostic and Prognostic Assays

The invention provides a method for detecting the presence of GRP in a biological sample. The method involves contacting the biological sample with an agent capable of detecting GRP protein or mRNA such that the presence of GRP is detected in the biological sample. A preferred agent for detecting GRP mRNA is a labeled or labelable nucleic acid probe capable of hybridizing to GRP mRNA. The nucleic acid probe can be, for example, the full-length GRP cDNA of SEQ ID NO: 1, or a portion thereof, such as an oligonucleotide of at least 15, 30, 50, 100, 250 or 500 nucleotides in length and sufficient to specifically hybridize under stringent conditions to GRP mRNA. A preferred agent for detecting GRP protein is a labeled or labelable antibody capable of binding to GRP protein. Antibodies can be polyclonal, or more preferably, monoclonal. An intact antibody, or a fragment thereof (e.g., Fab or $F(ab')_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect GRP mRNA or protein in a biological sample in vitro as well as in vivo. For example, in vitro techniques for detection of GRP mRNA include Northern hybridizations and in situ hybridizations. In vitro techniques for detection of GRP protein include enzyme linked immunosorbent assays (ELISAs), Western blots, immunoprecipitations and immunofluorescence. Alternatively, GRP protein can be detected in vivo in a subject by introducing into the subject a labeled anti-GRP antibody. For example, the antibody can be labeled with a radioactive marker whose presence and location in a subject can be detected by standard imaging techniques.

Accordingly, the invention provides a diagnostic method comprising:

contacting a sample from a subject with an agent capable of detecting GRP protein or mRNA;

determining the amount of GRP protein or mRNA expressed in the sample;

comparing the amount of GRP protein or mRNA expressed in the sample to a control sample; and forming a diagnosis based on the amount of GRP protein or mRNA expressed in the sample as compared to the control sample.

The invention also encompasses kits for detecting the presence of GRP in a biological sample. For example, the kit can comprise a labeled or labelable agent capable of detecting GRP protein or mRNA in a biological sample; means for determining the amount of GRP in the sample; and means for comparing the amount of GRP in the sample with a standard. The agent can be packaged in a suitable container. The kit can further comprise instructions for using the kit to detect GRP mRNA or protein.

The diagnostic methods of the present invention are elaborated further below. In preferred embodiments, the methods can be characterized as comprising detecting, in a sample of cells from the subject, the presence or absence of a genetic lesion characterized by at least one of (i) an alteration affecting the integrity of a gene encoding a GRP-protein, or (ii) the mis-expression of the GRP gene. To illustrate, such genetic lesions can be detected by ascertaining the existence of at least one of (i) a deletion of one or more nucleotides from a GRP gene, (ii) an addition of one or more nucleotides to a GRP gene, (iii) a substitution of one or more nucleotides of a GRP gene, (iv) a gross chromosomal rearrangement of a GRP gene, (v) a gross alteration in the level of a messenger RNA transcript of a GRP gene, (vii) aberrant modification of a GRP gene, such as of the methylation pattern of the genomic DNA, (vii) the presence of a non-wild type splicing pattern of a messenger RNA transcript of a GRP gene, (viii) a non-wild type level of a GRP-protein, (ix) allelic loss of a GRP gene, and (x) inappropriate post-translational modification of a GRP-protein. As set out below, the present invention provides a large number of assay techniques for detecting lesions in a GRP gene, and importantly, provides the ability to discern between different molecular causes underlying GRP-dependent aberrant bioactivity of a GRP popypeptide.

In an exemplary embodiment a nucleic acid composition is provided which contains an oligonucleotide probe previously described. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) PNAS 91:360–364), the latter of which can be particularly useful for detecting point mutations in the GRP-gene (see Abravaya et al. (1995) Nuc Acid Res 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a GRP gene under conditions such that hybridization and amplification of the GRP-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In another embodiment of the subject assay, mutations in a GRP gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the GRP gene and detect mutations by comparing the sequence of the sample GRP with the corresponding wild-type (control) sequence. Exemplary sequencing reactions include those based on techniques developed by Maxim and Gilbert (Proc. Natl Acad Sci USA (1977) 74:560) or Sanger (Sanger et al (1977) Proc. Nat. Acad. Sci 74:5463). Any of a variety of automated sequencing procedures may be utilized when performing the subject assays (Biotechniques (1995) 19:448), including by sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one skilled in the art that, for certain embodiments, the occurence of only one, two or three of the nucleic acid bases need be determined in the sequencing reaction. For instance, A-tract sequencing where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1 985) Science 230:1242). In general, the art technique of "mismatch cleavage" starts by providing heteroduplexes formed by hybridizing (labelled) RNA or DNA containing the wild-type GRP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in GRPγ cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a GRP sequence, e.g., a wild-type GRP sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in GRP genes.

For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125–144; and Hayashi (1992) Genet Anal Tech Appl 9:73–79). Single-stranded DNA fragments of sample and control GRP nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al (1989) Proc. Natl Acad. Sci USA 86:6230). Such allele speicific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a GRP gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant GRP proteins, which are discussed, above, may also be used in disease diagnostics and prognostics. Such diagnostic methods, may be used to detect abnormalities in the level of GRP protein expression, or abnormalities in the structure and/or tissue, cellular, or subcellular location of GRP protein. Structural differences may include, for example, differences in the size, electronegativity, or antigenicity of the mutant GRP protein relative to the normal GRP protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of GRP proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the GRP protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody.

Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

Moreover, any of the above methods for detecting alterations in a GRP gene or gene product can be used to monitor the course of treatment or therapy.

VIII. Methods of Modulating Cell Adhesion

In another aspect, the present invention pertains to methods for modulating integrin-mediated attachment of a cell to extracellular matrices and cell-cell adhesion events. As used herein, the term "integrin" refers to a family of receptors comprising ab heterodimers that mediate cell attachment to extracellular matrices and cell-cell adhesion events. The a subunits vary in size between 120 and 180 kd and are each noncovalently associated with a b subunit (90–110 kd) (reviewed by Hynes, 1992). Most integrins are expressed in a wide variety of cells, and most cell express several integrins. There are at least 8 known b subunits and 14 known a subunits. The majority of the integrin ligands are extracellular matrix proteins involved in substratum cell adhesion such as collagens, laminin, fibronectin among others. However, some of these, such as fibrinogen, can also mediate cell-cell aggregation, whereas others recognize integral membrane proteins of the immunoglobulin superfamily (e.g., ICAM-1, ICAM-2, VCAM-2) and mediate direct cell-cell adhesion (reviewed by Hynes, 1992). In one embodiment, the GRP protein acts a potentiators of cell adhesion by an "inside-out signaling" phenomenon. The term "inside-out signaling" refers to the mechanisms by which intracellular signaling systems influence the affinity of receptors that interact with the surrounding matrix and thus influence the orderly attachment of cells to their surrounding matrix.

In one embodiment, methods for promoting the attachment (adhesion) of cells to a substrate are provided. Based on the ability of a GRP polypeptide to modulate the activity of an integrin molecule to its ligand, cell attachment or detachment to a substrate can be modulated.

The substrate can be any solid-matrix having a surface on which cell adhesion promoting activity is desired and includes without limitation containers for cell culture, medical devices, prosthetic devices, synthetic resin fibers, blood vessels or vascular grafts, percutaneous devices, artificial organs, and the like. The surface can additionally be comprised of glass, a synthetic resin, nitro cellulose, polyester, agarose, collagen or a long chain polysaccharide.

Also encompassed are prosthetic and medical devices that make use of the substrate to attach cells to the surface in vivo or to promote growth of cells on a particular surface prior to grafting.

In another embodiment, a method for selecting transfected cells is provided wherein a vector containing a gene encoding a GRP polypeptide is co-expressed with a second gene in a cell.

Transfected cells are expected to adhere more strongly to the substratum, thus facilitating the screening of the transfected cells.

IX. Methods of Modulating Cell Adhesion and Therapeutic Uses

Yet another aspect of the present invention features a method of modulating one or more of cell adhesion, membrane trafficking, insulin action on glucose transport of a cell by modulating GRP biological activity, e.g., by potentiating or disrupting certain protein-GRP interactions, ligand-GRP interaction. In general, whether carried out in vivo, in vitro, or in situ, the method comprises treating the cell with an effective amount of a GRP agent so as to alter, relative to the cell in the absence of treatment, at least one of (i) cell adhesion, (ii) membrane trafficking, or (iii) insulin action on glucose transport of a cell. As described herein, there are a wide variety of pathological conditions for which GRP modulating agents of the present invention can be used in treatment in a subject, including but not limited to, thrombosis, inflammation, cancer. As used herein the term "modulating agent" refers to any of the subject polypeptides or nucleic acid molecules, such as gene therapy constructs, antisense molecules, peptidomimetics. In addition a GRP modulating agent can be a compound identified in one of the drug assays provided herein. As used herein, a "patient" or "subject" to be treated can mean either a human or non-human animal.

The term "modulation" encompases both increasing and decreasing GRP activity. The terms "GRP activity", "GRP bioactive", or variations thereof are used interchangeably herein. In certain embodiments it will be desirable to inhibit or reduce GRP activity, such as with the subject antisense techniques. In other embodiments it will be desirable to increase or augment GRP activity in a cell, for example using the subject gene therepy techniques.

Accordingly, the method can be carried out with GRP agents such as peptide and peptidomimetics or other molecules identified in the above-referenced drug screens which agonize or antagonize the effects of signaling from a GRP protein or ligand binding of a GRP protein, e.g., an intracellular target molecule, e.g., an integrin molecule, PI-3,4,5. Other GRP agents include antisense constructs for inhibiting expression of GRP proteins, and different domains of the GRP proteins that may act as dominant negative mutants of GRP proteins which competitively inhibit ligand interactions upstream and signal transduction downstream of the GRP protein.

Since the subject GRP modulating agents can either increase or decrease GRP activity, the agents will be useful for stimulating or suppressing immune responses. In one embodiment, GRP modulating agents can be used to modulate inside out signaling of a hematopoietic cell including, but not limited to, the orderly attachment of lymphoid cells to their surrounding matrix, the adhesion of platelets to fibrinogen, the coupling of lymphocytes to their antigen presenting cells, and the phagocytosis of complement-opsonized targets by myelomonocytic phagocytes (reviewed by Diamond and Springer, 1994; Hynes 1992; Sastry and Horwitz, 1993).

In one embodiment, the subject method of modulating GRP bioactivity can be used to inhibit cell adhesion of lymphoid cells, e.g., T cells, natural killer cells, so as to inhibit immune reactions such as graft rejection, inflammation and homing of lymphocytes to inflamed areas. Other exemplary disorders that may benefit from modulation of GRP include, but are not limited to various immune-mediated disorders such as autoimmune disorders. The term disorder is meant to include both normal conditions that would benefit from an alteration in GRP activity and various disease states. For example, the subject modulating agents can be used to inhibit responses in clinical situations where it is desirable to downmodulate T cell responses. For example, in graft-versus-host disease, cases of transplantation, autoimmune diseases (including, for example, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scieroderma, vaginitis, proctitis, drug eruptions,leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis). Downmodulation of GRP will also be desirable in cases of allergy such as, atopic allergy.

In another embodiment, the subject method is used to modulate thrombosis by regulating the integrin-mediated adhesion of platelets to fibrinogen in a subject comprising the treatment of platelets with an agent that modulates integrin function. Unactivated platelets bind to the surface-bound fibrinogen via integrin aIIb3 and can thus join hemostatic events already underway. However, only after platelet activation by thrombin, collagen, or other platelet agonists does αIIβ3 become an effective receptor for fibrinogen (Kieffer, N. and D. R. Phillips (1990) *Annu. Rev. Cell Biol.* 6:329–57) or other ligands (Kieffer and Phillips (1990) supra; Phillips et al. (1991) *Cell* 65:359–62). Activation of aIIb3 can be accomplished by activation of platelets, an event that involves activation of several G proteins, increases the intracellular pH and calcium, phosphatidyl inositol turnover, and activation of protein kinases (Manning, D. R. and L. F. Brass (1991) *Thromb. Haemost.* 66:393–399; Shattil, S. J. and J. S. Brugge, (1991) *Curr. Opin. Cell. Biol.* 3:869–879). Thus, the GRP agents of the present invention can modulate platelet aggregation by regulating integrin αIIβ3 affinity for ligands such as fibrinogen during and thus may provide effective agent agents in the treatment of thrombosis. In a preferred embodiment the agent inhibits GRP cell adhesion stimulatory activity. Examples of such inhibitory agents include antisense GRP nucleic acid molecules, anti-GRP antibodies, dominant negative forms of GRP, for example, PH domain, among others. Although inhibitory agents are preferred embodiments, agents that stimulate GRP activities are also encompassed. Examples of such stimulatory agents include active GRP protein and a nucleic acid molecule encoding GRP that has been introduced into the cell. These modulatory methods can be performed in vitro (e.g., by culturing the cell with the agent) or, alternatively, in vivo (e.g, by administering the agent to a subject).

Another aspect of the invention pertains to methods of modulating GRP bioactivity associated within a cancer cell to inhibit, for example, adhesion of a metastatic cell. Acquisition of a metastatic phenotype by tumor cells is multistage process involving numerous aberrant functions of the tumor cell. These aberrant functions include tumor angiogenesis, attachment, adhesion to the vascular basement membrane, local proteolysis, degradation of extracellular matrix components, migration through the vasculature, invasion of the basement membrane, and proliferation at secondary sites (Poste, G. and Fidler, I. J. (1980) *Nature* 283:139–146; Liotta, L. A. et al. (1991) *Cell* 64:327–336). Invasion of malignant cells requires altered cellular interactions with extracellular matrix. Integrin-type cell adhesion receptors have been shown to play an important role in processes such as cancer cell migration, penetration through basement membranes and other molecular barriers (reviewed in Heino, Int J. Cancer). Integrin action in cancer cells can also be regulated by intracellular mechanisms by inside-out signalling, which is thought to take place by altering the conformation of extracellular domains through cytoplasmic domains (Heino, supra).

Thus, agents that interfere with the ability of cancer cell adhesion during these events may provide effective therapeutic agent in the treatment of cancer. In a preferred embodiment the agent inhibits GRP cell adhesion stimulatory activity. Examples of such inhibitory agents include antisense GRP nucleic acid molecules, anti-GRP antibodies, dominant negative forms of GRP, for example, PH domain. Although inhibitory agents are preferred embodiments, agents that stimulate GRP activities are also within the scope of the invention. Examples of such stimulatory agents include active GRP protein and a nucleic acid molecule encoding GRP that has been introduced into the cell. These modulatory methods can be performed in vitro (e.g., by culturing the cell with the agent) or, alternatively, in vivo (e.g, by administering the agent to a subject).

Inhibition of GRP activity is desirable in situations in which decreased integrin-mediated cell adhesion is likely to have a beneficial effect. As described above, one example of such a situation is in tumor cells, and in particular in inhibiting or preventing tumor cell metastatis. Thus, decreasing the expression and/or activity of GRP in tumor cells is expected to reduce the development or progression of the metastatic phenotype. Accordingly, in a specific embodiment, the invention provides a method for inhibiting development or progression of a metastatic phenotype in a tumor cell comprising contacting the tumor cell with an agent which decreases the amount or the activity of GRP in the tumor cell. The agent, preferably in a pharmaceutically acceptable carrier, can be administered to a tumor-bearing subject by an appropriate route to inhibit the development or progression of the metastatic phenotype of the tumor. Suitable routes of administration include intravenous, intramuscular or subcutaneous injection, injection directly into the tumor site or implantation of a device containing a slow-release formulation. The agent preparation can also be incorporated into liposomes or other carrier vehicles to facilitate delivery to the tumor site. A non-limiting dosage range is 0.001 to 100 mg/kg/day, with the most beneficial range to be determined by routine pharmacological methods.

Alternative to administration of GRP protein itself, the development or progression of the metastatic phenotype can be inhibited in tumor cells by modifying them to express GRP by introducing into the tumor cells a nucleic acid encoding GRP (e.g., via a recombinant expression vector). Expression vectors suitable for gene therapy, including retroviral and adenoviral vectors carrying appropriate regulatory elements, can be used to deliver the GRP-encoding nucleic acid to the tumor cells.

The ability of an agent, e.g., protein or DNA to inhibit tumor progression and/or metastatis can be evaluated using in vivo and in vitro assays known in the art.

In contrast to the foregoing situations in which inhibition of GRP activity is desirable, there are other situations in which it may be desirable to increase GRP activity.

In another embodiment, modulators of GRP expression are identified in a method wherein a cell is contacted with a test substance and the expression of GRP mRNA or protein in the cell is determined. The level of expression of GRP mRNA or protein in the presence of the test substance is compared to the level of expression of GRP mRNA or protein in the absence of the test substance. The test substance can then be identified as a modulator of GRP expression based on this comparison. For example, when expression of GRP RNA or protein is greater in the presence of the test substance than in its absence, the test substance is identified as a stimulator of GRP mRNA or protein expression. Alternatively, when expression of GRP RNA or protein is less in the presence of the test substance than in its absence, the test substance is identified as an inhibitor of GRP mRNA or protein expression. The level of GRP mRNA or protein expression in the cells can be determined by methods described above for detecting GRP mRNA or protein.

In still another embodiment, the subject method can be used to modulate trafficking across the membrane of cell surface proteins using GRP polypeptides or the SEC7 domain. The term "membrane trafficking" refers the intracellular translocation of a protein from the endoplasmic reticulum to the Golgi apparatus or from mature secretory vesicles to the plasma membrane. The identification of a SEC7 domain in a GRP polypeptide supports the possible role of these polypeptides in Golgi processing of secretory glycoproteins. SEC7 domains were originally identified in yeast as part of a large protein containing 2008 amino acids which was involved in membrane traffic from the yeast Golgi apparatus (Achstetter et al. (1988) *J. Biol. Chem.* 263(4): 11711–11717). Most of the SEC mutations block transport of proteins from the endoplasmic reticulum to the Golgi apparatus or from mature secretory vesicles to the plasma membrane. (Esmon, B. et al. (1981) *Cell* 25:451–60; Stevens, T. et al. (1982) *Cell* 30: 439–48; Riezman, H. (1985) *Cell* 40: 1001–09). Mutations that define the sec7 locus exert a unique and dramatic effect on traffic of secretory, plasma membrane, vacuolar, and endocytic marker molecules (Novick et al. (1980) supra; Esmon et al. (1981) supra). At the restrictive growth temperature, sec7 mutant cells accumulate secretory glycoproteins within the Golgi apparatus, leading to the exaggeration of Golgi cisternae. The finding that the GRP protein of the present invention contains a PH domain capable of binding to 3-phosphinositides and a SEC7 domain which, at least based on the yeast system, is involved in glycoprotein processing, provides a direct link between PI(3) kinase signalling and glycoprotein processing.

In a preferred embodiment, GRP bioactivity mediating membrane trafficking of a cell surface protein, such as a glucose transporter, can be modified. In a most preferred embodiment, GRP bioactivity is modulated in an insulin-sensitive cell, for example, an adipocyte or a muscle cell. Insulin stimulation of adipose and muscle cells results in rapid marked translocation of a GLUT glucose transport protein, e.g., the GLUT4 glucose transporter, to the cell surface. Acute stimulation of sugar uptake by insulin results from GLUT4 redistribution to the plasma membrane. Strong evidence implicates a direct role for PI(3) kinase activity in insulin-mediated translocation of the GLUT4 transporters to the cell membrane (6). The finding that the GRP protein of the present invention contains a PH domain capable of binding to 3-phosphinositide and a SEC7 domain which, at least based on the yeast system, is involved in glycoprotein processing, provides a direct link between PI(3) kinase signalling and glycoprotein processing and presumably mediates the enhanced GLUT4 translocation to the surface of a cell.

Accordingly, in one embodiments, the present invention provides a method of modulating GRP bioactivity in regulating the translocation of a glucose transporter to the surface of an insulin-sensitive cell, e.g., an adipocyte or a muscle cell. For instance, the present method can be used to regulate the glucose transporter translocation that underlies the mechanism of insulin action to stimulate glucose uptake into cells.

In a preferred embodiment, the glucose transporter molecule is a member of the facilitative glucose transporter family (GLUT) of glucose carriers (reviewed in Czech, M. P.(1995) *Annu. Rev. Nutr.* 15: 441–71. The glucose transporter protein is GLUT4 which is present in insulin-sensitive adipocytes and muscle cells (67, 116). This protein is one of five mammalian hexose transporters (GLUT1–5, which show 39–65% sequence identities in humans by paired comparison) (for review see 128). GLUT4 appears to mediate virtually all of the insulin-stimulated glucose uptake in model systems containing both isoforms, whereas GLUT1 contributes significantly to basal hexose transport (57, 153).

In one preferred embodiment, the subject method enhances GRP activity, which increases the processing of GLUT4, thus enhancing the amount of GLUT4 present at the surface of a cell. Accordingly, the method can be carried out with a GRP agent, such as a peptide of a peptidomimetic or other molecules identified in the above-referenced screens which agonize the effects of signaling from a GRP protein, e.g., an intracellular target molecule, e.g., a PI-3,4,5, or a downstream effector, or antagonize the action of an antagonist of GRP activity. Other GRP agents include constructs expressing GRP proteins or portions thereof, agents which upregulate the expression of an endogenous GRP protein among others. In one preferred embodiment, GRP therapeutics can be used in the treatment of diseases having altered glucose metabolism, such as Type 2 diabetes.

In another embodiment, GRP therapeutics that antagonize the effects of signaling from a GRP protein are provided. Thus, peptide of a peptidomimetic or other molecules identified in the above-referenced screens which antagonize the effects of signaling from a GRP protein, e.g., an intracellular target molecule, e.g., a PI-3,4,5, or a downstream effector can be used. According to this embodiment, other GRP therapeutics including antisense constructs for inhibiting the expression of GRP proteins, and different domains of the GRP protein that may act as dominant negative regulators of GRP activity are included.

X. Method of Cloning Phospholipid Binding Proteins

In another aspect, the invention features a method of cloning phospholipid binding proteins by an expression library screening using labeled phospholipids. A preferred embodiment is described in Example 1, wherein expression libraries can be screened using phospholipid probes. The probe includes a detectable label group attached thereto. The expression system can be used to screen for phospholipid binary proteins.

In a preferred embodiment, cDNA libraries are constructed in expression vectors such as XgtII, Xgt 18–23, λZAP and λORF8. Messenger libraries of this type, having coding sequences in the correct reading frame and orientation, can be used to express a given clone. In other embodiments, the clone can be expanded as a fusion protein. For instance, λgtII will produce fusion proteins whose amino termini consist of β-galactosidase amino acid sequences and whose carboxy termini consist of a foreign polypeptide. Phospholipid binding proteins, e.g., other orthologs of a particular GRP protein or other paralogs from the same species, can then be detected with labeled phospholipids as for example, reacting nitrocellulose filters lifted from infected plates with labeled 3-phosphoinositides, e.g. PI(3)P, PI(3,4)P and PI(3,4,5)P. Thus the presence of GRP homologs can be detected and cloned from other species, e.g. humans, as can alternate isoforms (including splicing variants) from mice.

In another embodiment, it will be desirable to attach a label group to a probe, e.g. a phospholipid, a polypeptide, to facilitate detection. The label group can be selected from a group consisting of radioisotopes, fluorescent compounds, enzymes and enzyme co-factors. In a preferred embodiment, phospholipids can be labeled with radiolabeled ATP in the presence of a kinase, e.g. PI-3 kinase. Reaction products can be detected by HPLC analysis. The radioactivity isotope can also be detected by such means as the use of a γ counter or a scintillation counter by autoradiography.

In one embodiment, it is desirable to attach a label group to the subject probe to facilitate detection. One means for labeling a probe, e.g., a polypeptide, is via linkage to an enzyme. The enzyme which is bound to the probe will react with an appropriate substrate, preferably a chromogenic substrate, in such a manner as to produce a chemical moiety which can be detected, for example, by spectrophotometric, fluorimetric or by visual means. Enzymes which can be used to detectably label the probe include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

It is also possible to label the probes with a fluorescent compound. When the fluorescently labeled antibody is exposed to light of the proper wavelength, its presence can then be detected. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

The probe also can be detectably labeled by coupling it to a chemiluminescent compound. The presence of the chemiluminescent-tagged antibody is then determined by detecting luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the probe of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

This invention is further illustrated by the following examples which should not be construed as limiting. The contents of all references, patents and published patent applications cited throughout this application are hereby incorporated by reference.

EXAMPLE 1

Signaling by 3,4,5-Phosphoinositide through PH Domains of Integrin Regulator Proteins Experimental Procedures $^{32}$P-labeled Phospholipids Probes to Screen Libraries The 3'-phosphatidylinositol probes labeled at the 3' position were generated using GST-p110 PI 3-kinase purified from recombinant bacculovirus infected Sf 9 cells using either purified phosphatidylinositol phosphates or crude brain lipid. Briefly, 20 mg phospholipid in chloroform was dried under $N_2$ and resuspended in 30 ml of buffer containing Tris-HCl pH 7.4, EDTA 1 mM and incubated in 200 ml phopsphorylation media containing 20 mM Tris-HCl pH 7.4, 100 mM NaCl, 10 mM $MgCl_2$, 0.5 mM EGTA. 0.2 mM adenosine, GST-p110 and 5–10 mCi [g-$^{32}$P]ATP (5 Ci/umol). The reaction was carried out for 2 h at room temperature, quenched by addition of 0.2 ml of 1M HCl, followed by 0.5 ml of chloroform:methanol (1:1). The organic phase containing phospholipids was washed 4 times with 0.4 ml of methanol:HCl (1:1) and stored at −70° C. until use. Just before use, the lipid was dried under a stream of nitrogen with phosphatidyl serine corresponding to a final concentration of 20 mg/ml. The identities of the PI 3-P, PI 3,4-$P_2$ and PI 3,4,5-$P_3$ were confirmed by TLC and HPLC analysis.

Library Screening

Mouse 3T3-FA442A (kind gift of Dr. Bruce Spiegelman) and mouse brain expression libraries were plated and protein expression induced by standard techniques. Briefly, 40,000 pfu of the cDNA libraries were plated on each of eighteen 15 cm plates and incubated for 4 h at 42° C. Nitrocellulose filters that had been soaked in 10 mM isopropylthio-b-D-galactoside and subsequently dried were placed on the filters, and incubation was continued for 14–16 h at 37° C. The plates were cooled to 4° C. and filters were removed and washed 3–4 times in 300 ml assay buffer (25 mM tris pH 7.4, 100 NaCl, 0.25% nonidet P-40, 0.1% sodium cholate, 1 mM $MgCl_2$, 0.5% dithiotreitol) under constant agitation. The filters were then incubated for 30 minutes in a crystallization bowl with the dissolved lipid in 30 ml assay buffer at room temperature with 2 Ci/ml of labeled mixed brain lipid and shaken vigorously. The filters were washed with five changes of the same buffer, dried and subjected to autoradiography. The primary screen was performed in 15 cm dishes and the subsequent screens in 10 cm dishes Binding Assays To generate the GST fusion proteins, PCR reactions using the primers:

GGAATTCCTTCGGCACGAGCGGTG and
CCGCTCGAGCGGTGGCTATTTGCTTGTTCCTC for the GST-N construct,
GGAATTCCGACAACCTGACTTCAGTGG and
CCGCTCGAGCGGTGTGTGTCAGGTCATTTCC for the GST-Sec7 construct,
GGAATTCCTATGAAAGTATCAAGAATGAGC and
CCGCTCGAGCGGCTGGATCCTGACATTTACC for the GSTPH construct, and
GGAATTCCTTCGGCACGAGCGGTG and
CCGCTCGAGCGGCTGGATCCTGACATTTACC for the GSTGRP constructs. The sequences of the PCR products were verified, and cloned into pGEX-5X-3 in the ECoR1 and Xba 1 sites. The bacteria were lysed and the fusion proteins were bound to gluthathione agarose according to standard procedures. Elution was effected by incubation of the beads with one volume 20 mM Hepes, 100 mM NaCl, 1 mM dithiotreitol (H buffer) supplemented with 10 mM gluthatione and 1% sodium cholate, and the eluate was dialyzed extensively against H buffer. For binding assays, protein was bound to nitrocellulose using a BIO-RAD BIO-DOT™ apparatus, using 150 pmol per well for binding assays and 7.5 pmol for competition assays. The nitrocellulose was washed in assay buffer, and 3 mm circles of the filters containing the protein were cut out and incubated in 40 ml assay buffer with the relevant lipids and competitors for 2 h under constant agitation. The filters were washed four times with 1 mL assay buffer and counted in a scintillation counter.

Figure 2A:
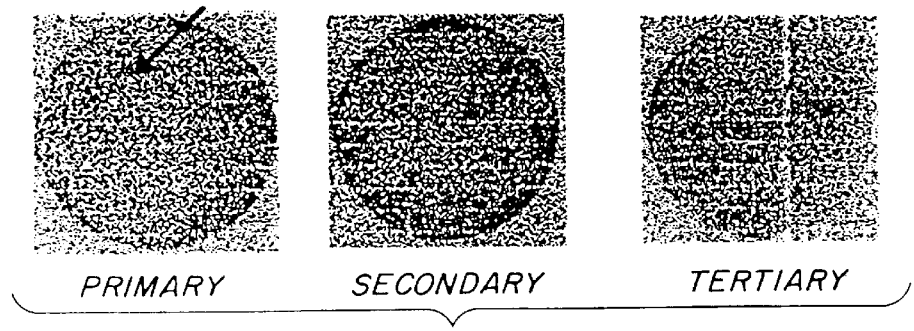
FIG. 2 shows the expression cloning of GRP cDNA. (A) Autoradiographs of nitrocellulose filters at different stages of purification of the cDNA clone identified in a mouse adipocyte cDNA expression library. Filters were incubated with the mixed brain phosphoinositides labeled at the 3-position with the p110 PI-3 kinase and [$_{γ32}$P]ATP, and then washed. (B) Binding specificity of the isolated cDNA clone. cDNA library (Con) or the isolated cDNA clone were incubated with either [$^{32}$P]PI(3)P, [$^{32}$P]PI(3,4)P$_2$, or [32P] PI(3,4,5)P$_3$. (C) Densitometry of the autoradiograph shown in (B).
Figure 2B:
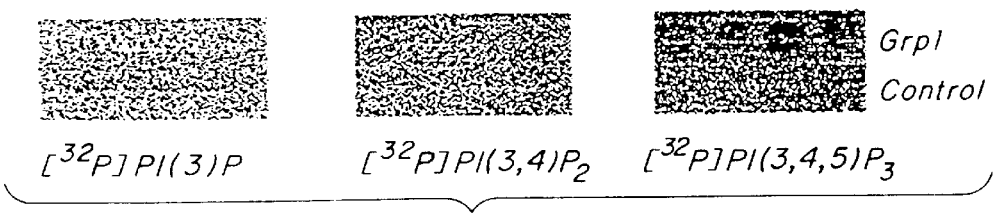

In order to identify such general receptors for phosphoinositides, GRPs, an expression library screening procedure was developed using brain phospholipids labeled with [$\gamma$-$^{32}$P]ATP in the presence of GSTp110 PI-3kinase. HPLC analysis of the reaction products confirmed the presence of $^{32}$P labeled PI(3)P, PI(3,4)P, and PI(3,4,5)P in this probe mixture. FIG. 1 shows the results of screening mouse 3T3-FA442A adipocyte and brain cDNA expression libraries with the labeled brain phosphoinositide. A single clone from each cDNA library screen reproducibly bound $^{32}$P label from the probe mixture upon subcloning and plaque purification (FIG. 2A). Approximately 1000 pfu of the cDNA library (Con) or the isolated cDNA clone were spotted on plates containing a lawn of E. Coli and incubated with nitrocellulose filters as described. The filters were incubated with 0.5×10$^6$ cpm of either [$^{32}$P]PI(3)P, [$^{32}$P]PI(3,4)P$_2$, or [32P]PI(3,4,5)P$_3$, processed as described above, and subjected to autoradiography. (C) Densitometry of the autoradiograph shown in (B). The values are the means of four determinations, and the error bars represent the standard deviations. Similar results were obtained using a mouse brain cDNA expression library. Importantly, the proteins encoded by both brain and adipocyte cDNA clones bound [$^{32}$P]PI(3,4,5)P$_3$ but not [$^{32}$P]PI(3,4)P$_2$ or [$^{32}$P]PI(3)P using the experimental conditions of the library screening procedure (FIG. 2B). Thus, this method can be used to identify phospholipid binding proteins with high sensitivity and specificity.

Figure 2C:
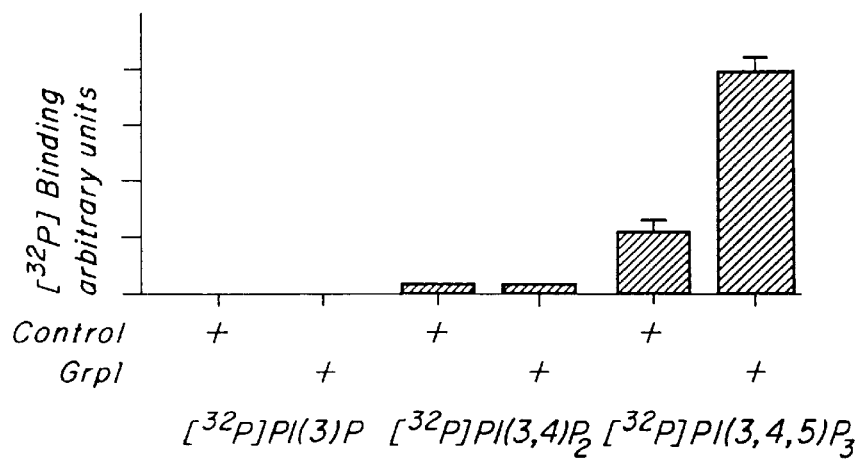
Figure 3A:
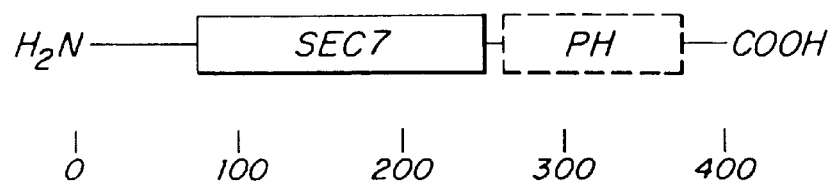
FIG. 3 is a schematic representation of the structure of GRP. (A) Overall structure of GRP and cytohesin-1 (CH-1). (B) Comparison of the deduced sequences of GRP SEQ ID NO: 2, B2-1/cytohesin-1 SEQ ID NO: 4 and EST 01394 SEQ ID NO: 3. The region corresponding to the Sec7 domain is boxed with a solid line, and the region corresponding to the PH domain is boxed with a dashed line.

Both brain and adipocyte cDNA clones identified in FIG. 2 were found to encode all but four residues of the amino acid sequence of the same novel protein GRP. Standard hybridization techniques were used to obtain additional cDNA clones of this species that encode a putative N-terminal methionine, and a full length sequence was deduced (FIG. 3). Database searched showed GRP to be highly similar to a protein encoded by the human cDNA, B2-1, originally cloned from cytolytic NCH/T cells (20). Both GRP and the B2-1-encoded protein contain two domains that are similar to those present in many other proteins; a pleckstrin homology domain (Lemmon et al. (1995) supra) and a Sec7 homology region (FIG. 3A). A report identified the B2-1 encoded protein (denoted cytohesin 1) based on its high affinity binding of the integrin β2 cytoplasmic domain through this Sec7 homology region (Liu, L. and B. Pohajdak (1992) supra; Kolanus et al. (1996) supra). Partial sequence of another probable isoform (Cts18) was also reported (23). The divergent amino acid sequences between GRP and cytohesin 1 or Cts18 are not due to species variation because a human EST found in the TIGR database show a predicted amino acid sequence identical to our mouse GRP between residues 34 and 120 (FIG. 2B). This EST differs in (19 amino acid differences out of 84) from the cytohesin-1/132-1 and out of 84 from the Cts 18 sequence. Based on these data and other similar EST sequences in the databases, it is likely that additional human isoforms of these proteins exist.

Mouse GRP shares several structural features with human cDNAs named B2-1 (cloned from natural killer cells and cytotoxic T cells)/cytohesin-1 (cloned from Jurkat T cell line) and a related cDNA cts18 (Liu, L. and B. Pohajdak (1992) supra; Kolanus et al. (1996) supra). Human B2-1/cytohesin-1 (a.a. 45–254) and cts18 contain a SEC7 domain approximately 42% identical to a 210 amino acid overlap to the yeast SEC7 domain (a.a. 811–1020) and 23% homology to the consensus 120 amino acid PH domain (Liu, L. and B. Pohajdak (1992) supra; Kolanus et al. (1996) supra). Mouse GRP shares approximately 85% identity to the full length B2-1/cytohesin. A comparison of the different domains as shown in FIG. 3 indicates approximately 89% identity with the SEC7 domains of B2-1/cytohesin-1 and 90% identity in the PH domain domain. The divergent amino acid sequences between GRP and B2- 1/cytohesin-1 are not due to species variation since a human EST found in the TIGR database shows a predicted amino acid sequence identical to the mouse GRP between residues 34 to 120 (FIG. 3B; SEQ ID NO:2), This EST differs in 19 amino acid differences out of 84) (77.4% identity) from the B2-1/cytohesin and cts18 sequence. The sequence comparison is shown in FIG. 3B.

Figure 4C:
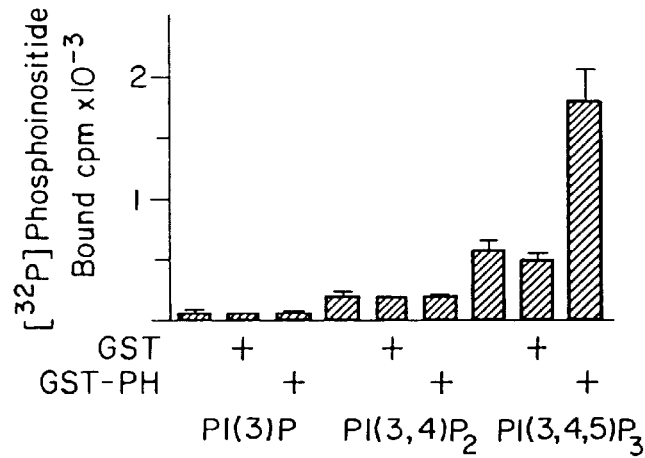

In order to determine whether PI(3,4,5)P$_3$ binding could be localized to specific sequences within the GRP structure, GST fusion proteins containing either residues 239 to 399 (PH domain), residues 52 to 260 (Sec7 domain), or residues 5 to 71, full length GRP residues 5–399 were expressed in bacteria and purified on glutathione-conjugated beads. Incubation of GST fusion proteins containing full length GRP or its PH domain with [$^{32}$P]PI(3,4,5)P$_3$ (24) resulted in extensive binding of the phospholipid (FIG. 4B). 150 pmol of the proteins were spotted on nitrocellulose filters, incubated with [$^{32}$P]PI(3,4,5)P$_3$ and the amount of bound lipid was determined as described. The values are the means of the quadruplicate determinations, and the error bars are the standard deviations. FIG. 4C shows the binding specificity of the PH domain of GRP. Nitrocellulose filters with GST-PH were incubated with 25,000 cpm of each of the phospholipids and the amount of bound lipid determined as described above. The values are the means of quadruplicate determinations and the error bars are the standard deviations. No significant binding of the [$^{32}$P]-labeled polyphosphoinositide by the fusion proteins containing the Sec7 homology region or residues 5 to 71 was observed over that of GST protein alone. Consistent with the results of FIG. 1 using the full length GRP cDNA expression clone, the GRP PH domain associates with [$^{32}$P]PI(3,4,5)P$_3$ specifically, since it failed to bind [$^{32}$P]PI(3,4)P$_2$ or [$^{32}$P]PI(3)P to a greater extent than GST(FIG. 4C). Although previous work has shown that PH domain from PLCδ (Lemmon et al. (1995) supra) and various other proteins (26) bind 4,5-polyphosphoinositide, none have been reported to preferentially associate with a 3-polyphosphoinositide. We further tested this unique specificity of the GRP PH domain using GST fusion proteins containing the Son of Sevenless and IRS-1PH domains in the same [$^{32}$P] polyphosphoinositide binding assay. These experiments confirmed that binding of [$^{32}$P]PI(3,4,5,)P$_3$ by the latter PH domains is negligible (FIG. 5).

The specificity of the GRP PH domain for binding [$^{32}$P] PI(3,4,5,)P$_3$ was also examined with respect to competition by the inositol phosphate head groups of the phosphoinositides. FIG. 5A shows that 100 μm of unlabeled inositol 1,3,4,5-P$_4$ markedly inhibited [$^{32}$P]3,4,5-phosphoinositide binding to GSTPH$_{(GRP)}$ whereas inositol 1,4,5 P$_3$ inositol 1,3,4,6-P$_4$, and inositol 1,2,5,6-P$_4$ had little or no effect at the same concentration. More specifically, 25,000 cpm of

[$^{32}$P]PI(3,4,5)P$_3$ was incubated with varying concentrations of inositol 1,3,4,5P$_4$ and bound radioactivity determined. The amount of radioactivity bound was calculated as percent of that bound in the absence of competitor. The values are means of quadruplicate measurements, and the error bars are standard deviations. The lack of inhibition by the latter two phosphoinositides is particularly striking since they carry the same charge as the inhibitor inositol 1,2,3,4-P$_4$ The concentration of inositol 1,3,4,5-P$_4$ that inhibited binding of [$^{32}$P]PI(3,4,5,)P$_3$ half maximally was about 3-6 μM (FIG. 5A). Taken together, the data in FIGS. 4 and 5 indicate extraordinary specificity of the GRP PH domain for PI(3,4,5)P$_3$. Panel B shows the specificity of [$^{32}$P]PI(3,4,5)P$_3$ binding to the PH domains of GRP. The binding to GST fusion proteins containing amino acids 462–569 of murine Sos or amino acid 13–115 of murine IRS-1 was assayed using 150 pmoles of protein bound to the filters. Competition of binding to 7.5 pmoles of GST-PH was measured in the presence of 100 μM of the competitors. The values were calculated as in (A), and are means of quadruplicate measurements and the error bars represent standard deviations. Analysis of the amino acid sequences of the GRP PH domain in comparison to the IRS-1 and Son of Sevenless PH domains (FIG. 5C) shows an additional lysine at position 273 and a unique lysine 282, arginine 283, arginine 284 motif in the N-terminal region, known to be important for 4,5-polyphosphoinositide binding in other PH domains (26). The hypothesis that these basic residues are important for PI(3,4,5)P$_3$ binding will require testing by direct structural analysis of the GRP PH domain in contact with PI(3,4,5)P$_3$ or its head group.

The remarkable selectivity of the GRP PH domain in binding PI(3,4,5)P$_3$ reveals its likely function is the recruitment of GRP to sites of PI(3,4,5)P$_3$ synthesis in response to the action of the receptor-regulated p110-typePI-3 kinases. Such recruitment the cytohesin-1/GRP proteins to specific cell membrane domains would localize their function, presumably mediated through their Sec7 homology regions. One such function of this domain, recently reported by (Kolanus et. al) (23) is enhancement of cellular adhesion through direct association with the cytoplasmic region of integrin β2. Transfection of Jurkat cells with the B2-1/cytohesin-1 cDNA or cDNA encoding the Sec7 homology domain alone enhanced their adhesion to ICAM-1, a known ligand of integrins containing β 2 chain, 10–50 fold. This effect was of similar magnitude as that mediated by the T cell receptor (23). No effects, of such transfections were observed on integrin α4β1-mediated cell binding to VCAM-1 indicating a specificity for β2 integrins. These recent findings together with the data presented here suggest a model in which receptor activated PI-3 kinase generates PI(3,4,5)P$_3$ at the plasma membrane which in turn localizes cytohesin 1/GRP related proteins to function as integrin β2 regulators (FIG. 6). According to this model, cell adhesion is enhanced through cytohesin/GRP-mediated increased affinity of the integrin receptors or by their clustering in the surface membrane. Consistent with this model, overexpression of the cytohesin-1 PH domain in Jurkat cells disrupted receptor-mediated cell adhesion to the integrin β2 ligand ICAM-1. In keeping with our present data demonstrating the unique binding specificity of [$^{32}$P]PI(3,4,5,)P$_3$ for the GRP PH domain, other expressed PH domains were not able to disrupt Jurkat cell adhesion to ICAM-1 (23). Further, the potent PI-3 kinase inhibitor wortmannin reportedly inhibits receptor-regulated cell adhesion, as expected for the mechanism proposed in FIG. 6. These considerations indicate that the cytohesin 1/GRP family proteins merge the PI-3 kinase signaling pathway with the modulation of cell adhesion through the integrin β2 protein, a function likely to have broad biological implications in many systems.

Additional References

1. Parker, P. J.(1994) *Curr. Biol.* 5:577; Wennstrom, S. et al. (1994) *Curr. Biol.* 4:385
2. Thelen, M. et al. (1995) *Biochem. Biophys. Res. Comm.* 217:1225; Kundra, V. et al. (1994) *Nature* 367:474
3. Bonnema, J. D. et al. (1994) *J. Exp. Med* 180:1427; Yano, H. et al. (1993) *J. Biol. Chem.* 268:25846
4. Okada, T. et al. (1994) *J. Biol. Chem.* 269:3568; Kanai, F. et al. (1993) *Biochem. Biophys. Res. Commun.* 195:762
5. Joly, J. et al. (1994) *Science* 263:684
6. Zell, T. et al. (1996) *J. Immun.* 156:883; Shimuzu, Y. et al. (1995) *J. Cell. Biol.* 131:1867
7. Harrison, S. A. et al. (1990) *J. Biol. Chem.* 265:20106–16
8. Holman, G. D. et al. (1990) *J. Biol. Chem.* 265:18172–79
9. Marette, A. et al. (1992) *Am. J. Physiol.* 263:C443–52
10. Mueckler, M. (1994) *Eur. J. Biochem.* 219:713–25
11. Robinson, R. et al. (1993) *J. Biol. Chem.* 268:22119–26

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

We claim:

1. An isolated protein which comprises an amino acid sequence at least 90% identical to the amino acid sequence of SEQ ID NO: 2, wherein said protein is capable of binding phosphoinositides.

2. The isolated protein of claim 1, comprising the amino acid sequence of SEQ ID NO: 2.

3. The isolated protein of claim 1, wherein the protein binds phosphotidylinositol-3,4,5 and is involved in cell adhesion.

4. The isolated protein of claim 1, wherein the protein binds phosphotidylinositol-3,4,5 and is involved in membrane trafficking.

5. An isolated protein comprising a PH domain which is at least 95% identical to a PH domain of the amino acid sequence of SEQ ID NO: 2, said PH domain being capable of binding phosphotidylinositol-3,4,5.

6. The isolated protein of claim 5, wherein said PH domain is the PH domain of SEQ ID NO: 2.

7. The isolated protein of claim 5, wherein said PH domain comprises amino acid residues 258 to 384 of SEQ ID NO: 2.

8. An isolated protein comprising a SEC7 domain which is at least 90% identical to a SEC7 domain of amino acid sequence of SEQ ID NO: 2, said SEC7 domain being capable of mediating cell adhesion.

9. The isolated protein of claim 8, wherein said SEC7 domain is the SEC7 domain of SEQ ID NO: 2.

10. The isolated protein of claim 8, wherein said SEC7 domain comprises amino acid residues 74 to 252 of SEQ ID NO: 2.

11. A pharmaceutical composition comprising a protein as in any of claims 1–10 and a pharmaceutically acceptable carrier.

12. A fusion protein comprising the protein of claim 1 operatively linked to a non-GRP polypeptide.

13. An isolated protein capable of binding phosphatidylinositol-3,4,5 encoded by a nucleic acid sequence capable of hybridizing to the nucleic acid of SEQ ID NO:1 in 6.0×SSC at 50° C. followed by washing in 0.2×SSC at 65° C.

14. An isolated protein comprising a PH domain encoded by a nucleic acid sequence comprising residues 772–1150 of SEQ ID NO:1, wherein said PH domain is capable of binding phosphatidylinositol-3,4,5.

15. An isolated protein comprising a SEC7 domain encoded by a comprising residues 217–754 of SEQ ID NO:1, wherein said SEC7 domain is capable of mediating cell adhesion.

* * * * *

```
                         SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: cDNA
```

(ix) FEATURE:
    (A) NAME/KEY: CDS
    (B) LOCATION: 1..1197

(xi) SEQUENCE DESCRIPTION: SEQ ID NO:1:

| | | | | | | | | | | | | | | | | |
|---|---|---|---|---|---|---|---|---|---|---|---|---|---|---|---|---|
| ATG | GAC | GAA | GGC | GGT | GGC | GGT | GAG | GGC | GGC | AGC | GTG | CCT | GAA | GAC | CTG | 48 |
| Met | Asp | Glu | Gly | Gly | Gly | Gly | Glu | Gly | Gly | Ser | Val | Pro | Glu | Asp | Leu | |
| 1 | | | | 5 | | | | | 10 | | | | | 15 | | |
| TCA | TTA | GAA | GAG | CGA | GAA | GAA | CTT | TTG | GAC | ATT | CGT | AGA | AGA | AAA | AAG | 96 |
| Ser | Leu | Glu | Glu | Arg | Glu | Glu | Leu | Leu | Asp | Ile | Arg | Arg | Arg | Lys | Lys | |
| | | | 20 | | | | | 25 | | | | | 30 | | | |
| GAA | CTT | ATT | GAT | GAC | ATT | GAG | AGG | CTG | AAA | TAT | GAA | ATT | GCA | GAA | GTG | 144 |
| Glu | Leu | Ile | Asp | Asp | Ile | Glu | Arg | Leu | Lys | Tyr | Glu | Ile | Ala | Glu | Val | |
| | | 35 | | | | | 40 | | | | | 45 | | | | |
| ATG | ACG | GAG | ATT | GAC | AAC | CTG | ACT | TCA | GTG | GAG | GAG | AGC | AAA | ACT | ACT | 192 |
| Met | Thr | Glu | Ile | Asp | Asn | Leu | Thr | Ser | Val | Glu | Glu | Ser | Lys | Thr | Thr | |
| | 50 | | | | | 55 | | | | | 60 | | | | | |
| CAG | AGG | AAC | AAG | CAA | ATA | GCC | ATG | GGA | AGG | AAG | AAA | TTC | AAC | ATG | GAC | 240 |
| Gln | Arg | Asn | Lys | Gln | Ile | Ala | Met | Gly | Arg | Lys | Lys | Phe | Asn | Met | Asp | |
| 65 | | | | | 70 | | | | | 75 | | | | | 80 | |
| CCC | AAA | AAG | GGC | ATT | CAG | TTC | CTA | ATT | GAG | AAC | GAC | CTG | CTG | CAG | AGC | 288 |
| Pro | Lys | Lys | Gly | Ile | Gln | Phe | Leu | Ile | Glu | Asn | Asp | Leu | Leu | Gln | Ser | |
| | | | | 85 | | | | | 90 | | | | | 95 | | |
| TCC | CCA | GAG | GAT | GTC | GCC | CAG | TTT | CTG | TAC | AAA | GGA | GAG | GGC | CTG | AAC | 336 |
| Ser | Pro | Glu | Asp | Val | Ala | Gln | Phe | Leu | Tyr | Lys | Gly | Glu | Gly | Leu | Asn | |
| | | | 100 | | | | | 105 | | | | | 110 | | | |
| AAG | ACC | GTC | ATC | GGA | GAC | TAC | CTG | GGT | GAG | AGG | GAT | GAC | TTT | AAT | ATC | 384 |
| Lys | Thr | Val | Ile | Gly | Asp | Tyr | Leu | Gly | Glu | Arg | Asp | Asp | Phe | Asn | Ile | |
| | | 115 | | | | | 120 | | | | | 125 | | | | |
| AAA | GTT | CTT | CAG | GCT | TTT | GTT | GAG | CTG | CAT | GAG | TTT | GCT | GAT | CTC | AAC | 432 |
| Lys | Val | Leu | Gln | Ala | Phe | Val | Glu | Leu | His | Glu | Phe | Ala | Asp | Leu | Asn | |
| | 130 | | | | | 135 | | | | | 140 | | | | | |
| CTT | GTC | CAG | GCC | TTA | AGG | CAG | TTC | CTA | TGG | AGC | TTC | AGA | CTT | CCT | GGA | 480 |
| Leu | Val | Gln | Ala | Leu | Arg | Gln | Phe | Leu | Trp | Ser | Phe | Arg | Leu | Pro | Gly | |
| 145 | | | | | 150 | | | | | 155 | | | | | 160 | |
| GAG | GCA | CAG | AAG | ATC | GAC | CGC | ATG | ATG | GAG | GCC | TTT | GCA | TCC | CGA | TAC | 528 |
| Glu | Ala | Gln | Lys | Ile | Asp | Arg | Met | Met | Glu | Ala | Phe | Ala | Ser | Arg | Tyr | |
| | | | | 165 | | | | | 170 | | | | | 175 | | |
| TGC | CTG | TGC | AAC | CCT | GGG | GTC | TTC | CAG | TCC | ACA | GAT | ACA | TGC | TAC | GTG | 576 |
| Cys | Leu | Cys | Asn | Pro | Gly | Val | Phe | Gln | Ser | Thr | Asp | Thr | Cys | Tyr | Val | |
| | | | 180 | | | | | 185 | | | | | 190 | | | |
| CTC | TCC | TTT | GCC | ATC | ATC | ATG | CTC | AAC | ACC | AGC | TTG | CAC | AAC | CAC | AAC | 624 |
| Leu | Ser | Phe | Ala | Ile | Ile | Met | Leu | Asn | Thr | Ser | Leu | His | Asn | His | Asn | |
| | | 195 | | | | | 200 | | | | | 205 | | | | |
| GTG | CGC | GAC | AAG | CCC | ACC | GCT | GAG | CGC | TTC | ATC | ACC | ATG | AAC | CGA | GGC | 672 |
| Val | Arg | Asp | Lys | Pro | Thr | Ala | Glu | Arg | Phe | Ile | Thr | Met | Asn | Arg | Gly | |
| | 210 | | | | | 215 | | | | | 220 | | | | | |
| ATC | AAC | GAG | GGT | GGG | GAC | CTT | CCT | GAG | GAG | CTG | CTG | AGG | AAC | TTG | TAT | 720 |
| Ile | Asn | Glu | Gly | Gly | Asp | Leu | Pro | Glu | Glu | Leu | Leu | Arg | Asn | Leu | Tyr | |
| 225 | | | | | 230 | | | | | 235 | | | | | 240 | |
| GAA | AGT | ATC | AAG | AAT | GAG | CCG | TTT | AAG | ATC | CCA | GAA | GAC | GAC | GGA | AAT | 768 |
| Glu | Ser | Ile | Lys | Asn | Glu | Pro | Phe | Lys | Ile | Pro | Glu | Asp | Asp | Gly | Asn | |
| | | | | 245 | | | | | 250 | | | | | 255 | | |
| GAC | CTG | ACA | CAC | ACG | TTC | TTC | AAC | CCA | GAC | CGA | GAA | GGC | TGG | CTG | CTG | 816 |
| Asp | Leu | Thr | His | Thr | Phe | Phe | Asn | Pro | Asp | Arg | Glu | Gly | Trp | Leu | Leu | |
| | | | | | 260 | | | | | 265 | | | | | 270 | |
| AAG | CTG | GGG | GGT | CGT | GTG | AAG | ACC | TGG | AAA | CGG | CGC | TGG | TTC | ATC | CTC | 864 |
| Lys | Leu | Gly | Gly | Arg | Val | Lys | Thr | Trp | Lys | Arg | Arg | Trp | Phe | Ile | Leu | |
| | | 275 | | | | | 280 | | | | | 285 | | | | |
| ACA | GAT | AAC | TGC | CTC | TAC | TAC | TTT | GAG | TAC | ACC | ACG | GAC | AAG | GAG | CCC | 912 |

```
                                                                              -continued Thr Asp Asn Cys Leu Tyr Tyr Phe Glu Tyr Thr Thr Asp Lys Glu Pro
        290                 295                 300

AGG GGC ATC ATC CCC CTG GAG AAC CTC AGC ATC AGG GAG GTG GAG GAC         960
Arg Gly Ile Ile Pro Leu Glu Asn Leu Ser Ile Arg Glu Val Glu Asp
305                 310                 315                 320

CCC CGG AAG CCG AAC TGC TTT GAG CTG TAT AAC CCC AGT CAC AAA GGT        1008
Pro Arg Lys Pro Asn Cys Phe Glu Leu Tyr Asn Pro Ser His Lys Gly
                325                 330                 335

CAA GTC ATC AAG GCC TGC AAG ACG GAG GCC GAT GGC CGT GTG GTG GAG        1056
Gln Val Ile Lys Ala Cys Lys Thr Glu Ala Asp Gly Arg Val Val Glu
                    340                 345                 350

GGC AAC CAC GTT GTG TAC CGG ATC TCT GCC CCC AGC CCG GAG GAA AAG        1104
Gly Asn His Val Val Tyr Arg Ile Ser Ala Pro Ser Pro Glu Glu Lys
                355                 360                 365

GAG GAG TGG ATG AAG TCC ATC AAA GCA AGC ATC AGT AGG GAC CCG TTC        1152
Glu Glu Trp Met Lys Ser Ile Lys Ala Ser Ile Ser Arg Asp Pro Phe
370                 375                 380

TAT GAC ATG TTG GCC ACG AGG AAA AGG AGG ATT GCC AAT AAG AAA            1197
Tyr Asp Met Leu Ala Thr Arg Lys Arg Arg Ile Ala Asn Lys Lys
385                 390                 395

TAG                                                                    1200

(2) INFORMATION FOR SEQ ID NO:2:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Glu Gly Gly Gly Gly Gly Ser Val Pro Glu Asp Leu
  1               5                  10                 15

Ser Leu Glu Glu Arg Glu Glu Leu Leu Asp Ile Arg Arg Lys Lys
                20                  25                 30

Glu Leu Ile Asp Asp Ile Glu Arg Leu Lys Tyr Glu Ile Ala Glu Val
                35                  40                 45

Met Thr Glu Ile Asp Asn Leu Thr Ser Val Glu Glu Ser Lys Thr Thr
    50                  55                  60

Gln Arg Asn Lys Gln Ile Ala Met Gly Arg Lys Lys Phe Asn Met Asp
65                  70                  75                  80

Pro Lys Lys Gly Ile Gln Phe Leu Ile Glu Asn Asp Leu Leu Gln Ser
                    85                  90                  95

Ser Pro Glu Asp Val Ala Gln Phe Leu Tyr Lys Gly Glu Gly Leu Asn
                100                 105                 110

Lys Thr Val Ile Gly Asp Tyr Leu Gly Glu Arg Asp Asp Phe Asn Ile
            115                 120                 125

Lys Val Leu Gln Ala Phe Val Glu Leu His Glu Phe Ala Asp Leu Asn
130                 135                 140

Leu Val Gln Ala Leu Arg Gln Phe Leu Trp Ser Phe Arg Leu Pro Gly
145                 150                 155                 160

Glu Ala Gln Lys Ile Asp Arg Met Met Glu Ala Phe Ala Ser Arg Tyr
                165                 170                 175

Cys Leu Cys Asn Pro Gly Val Phe Gln Ser Thr Asp Thr Cys Tyr Val
                180                 185                 190

Leu Ser Phe Ala Ile Ile Met Leu Asn Thr Ser Leu His Asn His Asn
            195                 200                 205
```

```
Val Arg Asp Lys Pro Thr Ala Glu Arg Phe Ile Thr Met Asn Arg Gly
    210                 215                 220
Ile Asn Glu Gly Gly Asp Leu Pro Glu Leu Leu Arg Asn Leu Tyr
225                 230                 235                 240
Glu Ser Ile Lys Asn Glu Pro Phe Lys Ile Pro Glu Asp Gly Asn
                245                 250                 255
Asp Leu Thr His Thr Phe Phe Asn Pro Asp Arg Glu Gly Trp Leu Leu
            260                 265                 270
Lys Leu Gly Gly Arg Val Lys Thr Trp Lys Arg Arg Trp Phe Ile Leu
            275                 280                 285
Thr Asp Asn Cys Leu Tyr Tyr Phe Glu Tyr Thr Thr Asp Lys Glu Pro
290                 295                 300
Arg Gly Ile Ile Pro Leu Glu Asn Leu Ser Ile Arg Glu Val Glu Asp
305                 310                 315                 320
Pro Arg Lys Pro Asn Cys Phe Glu Leu Tyr Asn Pro Ser His Lys Gly
                325                 330                 335
Gln Val Ile Lys Ala Cys Lys Thr Glu Ala Asp Gly Arg Val Val Glu
                340                 345                 350
Gly Asn His Val Val Tyr Arg Ile Ser Ala Pro Ser Pro Glu Glu Lys
            355                 360                 365
Glu Glu Trp Met Lys Ser Ile Lys Ala Ser Ile Ser Arg Asp Pro Phe
            370                 375                 380
Tyr Asp Met Leu Ala Thr Arg Leu Arg Arg Ile Ala Asn Lys Lys
385                 390                 395
```

(2) INFORMATION FOR SEQ ID NO:3:

(i) SEQUENCE CHARACTERISTICS:
        (A) LENGTH: 87 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

```
Leu Ile Asp Asp Ile Glu Arg Leu Lys Tyr Glu Ile Xaa Glu Val Met
1               5                   10                  15
Thr Glu Ile Asp Asn Leu Thr Ser Val Glu Glu Ser Lys Thr Thr Gln
                20                  25                  30
Arg Xaa Lys Gln Ile Ala Met Gly Arg Lys Lys Phe Asn Met Xaa Pro
            35                  40                  45
Lys Lys Gly Ile Gln Phe Leu Ile Glu Asn Asp Leu Leu Gln Ser Ser
        50                  55                  60
Pro Glu Asp Val Ala Gln Phe Leu Tyr Lys Gly Glu Gly Leu Asn Lys
65                  70                  75                  80
Thr Val Ile Gly Asp Tyr Leu
                85
```

(2) INFORMATION FOR SEQ ID NO:4:

(i) SEQUENCE CHARACTERISTICS:
        (A) LENGTH: 397 amino acids
        (B) TYPE: amino acid
        (D) TOPOLOGY: linear (ii) MOLECULE TYPE: peptide -continued (v) FRAGMENT TYPE: internal (xi) SEQUENCE DESCRIPTION: SEQ ID NO:4:

```
Met Glu Glu Asp Asp Ser Tyr Val Pro Ser Asp Leu Thr Ala Glu Glu
1               5                   10                  15

Arg Gln Glu Leu Glu Asn Ile Arg Arg Lys Gln Glu Leu Leu Ala
            20                  25                  30

Asp Ile Gln Arg Leu Lys Asp Glu Ile Ala Glu Val Ala Asn Glu Ile
                35                  40                  45

Glu Asn Leu Gly Ser Thr Glu Glu Arg Lys Asn Met Gln Arg Asn Lys
    50                  55                  60

Gln Val Ala Met Gly Arg Lys Lys Phe Asn Met Asp Pro Lys Lys Gly
65                  70                  75                  80

Ile Gln Phe Leu Ile Glu Asn Asp Leu Leu Lys Asn Thr Cys Glu Asp
                85                  90                  95

Ile Ala Gln Phe Leu Tyr Lys Gly Glu Gly Leu Asn Lys Thr Ala Ile
                100                 105                 110

Gly Asp Tyr Leu Gly Glu Arg Asp Glu Phe Asn Ile Gln Val Leu His
            115                 120                 125

Ala Phe Val Glu Leu His Glu Phe Thr Asp Leu Asn Leu Val Gln Ala
130                 135                 140

Leu Arg Gln Phe Leu Trp Ser Phe Arg Leu Pro Gly Glu Ala Gln Lys
145                 150                 155                 160

Ile Asp Arg Met Met Glu Ala Phe Ala Gln Arg Tyr Cys Gln Cys Asn
                165                 170                 175

Asn Gly Val Phe Gln Ser Thr Asp Thr Cys Tyr Val Leu Ser Phe Ala
            180                 185                 190

Ile Ile Met Leu Asn Thr Ser Leu His Asn Pro Asn Val Lys Asp Lys
    195                 200                 205

Pro Thr Val Glu Arg Phe Ile Ala Met Asn Arg Gly Ile Asn Asp Gly
    210                 215                 220

Gly Asp Leu Pro Glu Glu Leu Leu Arg Asn Leu Tyr Glu Ser Ile Lys
225                 230                 235                 240

Asn Glu Pro Phe Lys Ile Pro Glu Asp Asp Gly Asn Asp Leu Thr His
                245                 250                 255

Thr Phe Phe Asn Pro Asp Arg Glu Gly Trp Leu Leu Lys Leu Gly Gly
                260                 265                 270

Gly Arg Val Lys Thr Trp Lys Arg Arg Trp Phe Ile Leu Thr Asp Asn
            275                 280                 285

Cys Leu Tyr Tyr Phe Glu Tyr Thr Thr Asp Lys Glu Pro Arg Gly Ile
    290                 295                 300

Ile Pro Leu Glu Asn Leu Ser Ile Arg Glu Val Glu Asp Ser Lys Lys
305                 310                 315                 320

Pro Asn Cys Phe Glu Leu Tyr Ile Pro Asp Asn Lys Asp Gln Val Ile
                325                 330                 335

Lys Ala Cys Lys Thr Glu Ala Asp Gly Arg Trp Glu Gly Asn His Thr
                340                 345                 350

Val Tyr Arg Ile Ser Ala Pro Thr Pro Glu Glu Lys Glu Glu Trp Ile
            355                 360                 365

Lys Cys Ile Lys Ala Ala Ile Ser Arg Asp Pro Phe Tyr Glu Met Leu
            370                 375                 380

Ala Ala Arg Lys Lys Lys Val Ser Ser Thr Lys Arg His
385                 390                 395
```

(2) INFORMATION FOR SEQ ID NO:5:

(i) SEQUENCE CHARACTERISTICS:
       (A) LENGTH: 126 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:5:

```
Thr His Thr Phe Phe Asn Pro Asp Arg Glu Gly Trp Leu Leu Lys Leu
1               5                  10                 15
Gly Gly Arg Val Lys Thr Trp Lys Arg Arg Trp Phe Ile Leu Thr Asp
                20                 25                 30
Asn Cys Leu Tyr Tyr Phe Glu Tyr Thr Thr Asp Lys Glu Pro Arg Gly
                35                 40                 45
Ile Ile Pro Leu Glu Asn Leu Ser Ile Arg Glu Val Glu Asp Pro Arg
    50                 55                 60
Lys Pro Asn Cys Phe Glu Leu Tyr Asn Pro Ser His Lys Gly Gln Val
65                  70                 75                  80
Ile Lys Ala Cys Lys Thr Glu Ala Asp Gly Arg Val Val Glu Gly Asn
                85                 90                 95
His Val Val Tyr Arg Ile Ser Ala Pro Ser Pro Lys Glu Lys Glu Glu
                100                105                110
Trp Met Lys Ser Ile Lys Ala Ser Ile Ser Arg Asp Pro Phe
                115                120                125
```

(2) INFORMATION FOR SEQ ID NO:6:

(i) SEQUENCE CHARACTERISTICS:
       (A) LENGTH: 127 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:6:

```
Thr His Thr Phe Phe Asn Pro Asp Arg Glu Gly Trp Leu Leu Lys Leu
1               5                  10                 15
Gly Gly Gly Arg Val Lys Thr Trp Lys Arg Arg Trp Phe Ile Leu Thr
                20                 25                 30
Asp Asn Cys Leu Tyr Tyr Phe Glu Tyr Thr Thr Asp Lys Glu Pro Arg
                35                 40                 45
Gly Ile Ile Pro Leu Glu Asn Leu Ser Ile Arg Glu Val Glu Asp Ser
    50                 55                 60
Lys Lys Pro Asn Cys Phe Glu Leu Tyr Ile Pro Asp Asn Lys Asp Gln
65                  70                 75                  80
Val Ile Lys Ala Cys Lys Thr Glu Ala Asp Gly Arg Val Val Glu Gly
                85                 90                 95
Asn His Thr Val Tyr Arg Ile Ser Ala Pro Thr Pro Glu Glu Lys Glu
                100                105                110
Glu Trp Ile Lys Cys Ile Lys Ala Ala Ile Ser Arg Asp Pro Phe
                115                120                125
```

(2) INFORMATION FOR SEQ ID NO:7:

-continued

```
    (i) SEQUENCE CHARACTERISTICS:
        (A) LENGTH: 113 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

Gly Gln Cys Cys Asn Glu Phe Ile Met Glu Gly Thr Leu Thr Arg Val
1               5                   10                  15

Gly Ala Lys His Glu Arg His Ile Phe Leu Phe Asp Gly Leu Met Ile
                20                  25                  30

Cys Cys Lys Ser Asn His Gly Gln Pro Arg Leu Pro Gly Ala Ser Ser
            35                  40                  45

Ala Glu Tyr Arg Leu Lys Glu Lys Phe Phe Met Arg Lys Val Gln Ile
        50                  55                  60

Asn Asp Lys Asp Asp Thr Ser Glu Tyr Lys His Ala Phe Glu Ile Ile
65                  70                  75                  80

Leu Lys Asp Gly Asn Ser Val Ile Phe Ser Ala Lys Ser Ala Glu Glu
                85                  90                  95

Lys Asn Asn Trp Met Ala Ala Leu Ile Ser Leu Gln Tyr Arg Ser Thr
                100                 105                 110

Leu (2) INFORMATION FOR SEQ ID NO:8:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:8:

Thr Asp Gly Phe Ser Asp Val Arg Lys Val Gly Tyr Leu Arg Lys Pro
1               5                   10                  15

Lys Ser Met His Lys Arg Phe Phe Val Leu Arg Ala Ala Ser Glu Ala
                20                  25                  30

Gly Gly Pro Ala Arg Leu Glu Tyr Tyr Glu Asn Glu Lys Lys Trp Arg
            35                  40                  45

His Lys Ser Ser Ala Pro Lys Arg Ser Ile Pro Leu Glu Ser Cys Phe
        50                  55                  60

Asn Ile Asn Lys Arg Ala Asp Ser Lys Asn Lys His Leu Val Ala Leu
65                  70                  75                  80

Tyr Thr Arg Asp Glu His Phe Ala Ile Ala Ala Asp Ser Glu Ala Glu
                85                  90                  95

Gln Asp Ser Trp Tyr Gln Ala Leu Leu Gln Leu His Asn Arg Ala Lys
                100                 105                 110

Ala
```